United States Patent
Mangiardi

(10) Patent No.: US 11,865,021 B2
(45) Date of Patent: *Jan. 9, 2024

(54) BIDIRECTIONAL STENT AND METHOD OF USE THEREOF

(71) Applicant: Q3 MEDICAL DEVICES LIMITED, Dublin (IE)

(72) Inventor: Eric K. Mangiardi, Charlotte, NC (US)

(73) Assignee: Q3 MEDICAL DEVICES LIMITED, Dublin (IE)

( * ) Notice: Subject to any disclaimer, the term of this patent is extended or adjusted under 35 U.S.C. 154(b) by 342 days.

This patent is subject to a terminal disclaimer.

(21) Appl. No.: 15/638,599

(22) Filed: Jun. 30, 2017

(65) Prior Publication Data
US 2017/0354522 A1 Dec. 14, 2017

Related U.S. Application Data

(63) Continuation of application No. 15/165,917, filed on May 26, 2016, now Pat. No. 9,750,624, which is a
(Continued)

(51) Int. Cl.
*A61F 2/915* (2013.01)
*B23K 26/38* (2014.01)
(Continued)

(52) U.S. Cl.
CPC .............. *A61F 2/915* (2013.01); *B23K 26/38* (2013.01); *B23K 26/40* (2013.01);
(Continued)

(58) Field of Classification Search
CPC ............ A61F 2002/91558; A61F 2/915; A61F 2210/0014; A61F 2310/00023;
(Continued)

(56) References Cited

U.S. PATENT DOCUMENTS

| | | | |
|---|---|---|---|
| 5,449,373 A | | 9/1995 | Pinchasik et al. |
| 5,807,404 A | * | 9/1998 | Richter ..................... A61F 2/91 |
| | | | 623/1.16 |

(Continued)

FOREIGN PATENT DOCUMENTS

| | | |
|---|---|---|
| WO | 2002060350 | 8/2002 |
| WO | 2007053791 | 5/2007 |

OTHER PUBLICATIONS

Yuan et al., "Characterization of Poly(L-Lactic Acid) Fibers Produced by Melt Spinning," Journal of Applied Polymer Science, 2001, pp. 251-260, vol. 81.
(Continued)

*Primary Examiner* — Brian E Pellegrino
(74) *Attorney, Agent, or Firm* — Ping Wang; Rimon Law

(57) ABSTRACT

A bidirectional twistable stent is disclosed. The stent comprises a cylinder-shaped stent body having a plurality of axially arranged rows of struts encircling a central lumen and a plurality of flex connectors that connect at least two adjacent rows of struts in such a manner that allows the stent to be twisted clockwise or counter clockwise without causing deformation of any struts in the stent body. Also disclosed are the method of making the stent, method of using the stent, and a kit containing the stent.

5 Claims, 19 Drawing Sheets

Related U.S. Application Data continuation of application No. 14/163,728, filed on Jan. 24, 2014, now Pat. No. 9,375,810.

(51) Int. Cl.
  *B23K 26/40* (2014.01)
  *B23K 101/06* (2006.01)
  *B23K 103/14* (2006.01)

(52) U.S. Cl.
  CPC ............ *A61F 2002/91558* (2013.01); *A61F 2002/91566* (2013.01); *A61F 2002/91575* (2013.01); *A61F 2210/0004* (2013.01); *A61F 2210/0014* (2013.01); *A61F 2230/0069* (2013.01); *A61F 2230/0071* (2013.01); *A61F 2240/001* (2013.01); *A61F 2310/00023* (2013.01); *B23K 2101/06* (2018.08); *B23K 2103/14* (2018.08)

(58) Field of Classification Search
  CPC ...... A61F 2250/0018; A61F 2250/0029; A61F 2250/0037; A61F 2/82; A61F 2230/0069; A61F 2230/001
  USPC ........................................................ 623/1.22
  See application file for complete search history.

(56) References Cited

U.S. PATENT DOCUMENTS

| | | | |
|---|---|---|---|
| 5,911,754 A | 6/1999 | Kanesaka et al. | |
| 6,299,635 B1 | 10/2001 | Frantzen | |
| 6,443,982 B1 | 9/2002 | Israel et al. | |
| 7,867,272 B2 | 1/2011 | Niermann | |
| 7,985,251 B2* | 7/2011 | Ikeuchi | A61F 2/91 623/1.15 |
| 9,375,810 B2* | 6/2016 | Mangiardi | A61F 2/915 |
| 2002/0165605 A1 | 11/2002 | Penn | |
| 2004/0024444 A1* | 2/2004 | Moore | A61F 2/915 623/1.15 |
| 2004/0029446 A1 | 2/2004 | Ooya et al. | |
| 2004/0098118 A1* | 5/2004 | Granada | A61F 2/915 623/1.42 |
| 2004/0133271 A1 | 7/2004 | Jang | |
| 2004/0267353 A1 | 12/2004 | Gregorich | |
| 2005/0123582 A1 | 6/2005 | Sung et al. | |
| 2005/0288769 A1* | 12/2005 | Globerman | A61F 2/915 623/1.15 |
| 2006/0036315 A1 | 2/2006 | Yadin et al. | |
| 2007/0191927 A1 | 8/2007 | Bowe | |
| 2010/0131044 A1* | 5/2010 | Patel | A61F 2/915 623/1.16 |
| 2011/0160833 A1 | 6/2011 | Gonzalez et al. | |
| 2011/0190871 A1* | 8/2011 | Trollsas | A61F 2/915 623/1.15 |
| 2011/0230957 A1* | 9/2011 | Bonsignore | A61F 2/915 623/1.16 |
| 2012/0165921 A1 | 6/2012 | Casey | |
| 2012/0296362 A1* | 11/2012 | Cam | A61F 2/915 606/191 |
| 2013/0090721 A1 | 4/2013 | Bales | |
| 2013/0123905 A1* | 5/2013 | Abunassar | A61F 2/915 623/1.16 |
| 2013/0338761 A1 | 12/2013 | Plowiecki et al. | |

OTHER PUBLICATIONS

"Electrospinning—Fibers at the Nano-scale," Zeus Technical Newsletter, 2009, pp. 1-7.

McNaney, J.M. et al., "An experimental study of the superelastic effect in a shape-memory Nitinol alloy under biaxial loading", Mechanics of Materials, 2003, pp. 969-986.

File history of U.S. Appl. No. 14/163,728, filed Jan. 24, 2014.

File history of U.S. Appl. No. 15/165,917, filed May 26, 2016.

\* cited by examiner

BIDIRECTIONAL STENT AND METHOD OF USE THEREOF

This application is a Continuation of U.S. application Ser. No. 15/165,917, which is a Continuation of U.S. application Ser. No. 14/163,728, filed Jan. 24, 2014. Now U.S. Pat. No. 9,375,810. The entirety of the aforementioned application is incorporated herein by reference.

FIELD

The present application relates generally to medical devices and, in particular, to a stent implantable into a body cavity and method for implanting same.

BACKGROUND

An in vivo supporting device or barrier device, such as a stent, is a man-made "tube" or "frame" inserted into a natural passage or conduit in the body to prevent, or counteract, a disease-induced, localized flow constriction or flow outflow like a leak or aneurysm. Supporting stents include vascular supporting stents, non-vascular supporting stents, and aneurysm sealing stents. Vascular supporting stents are designed for applications in the vascular system, such as arteries and veins. Non-vascular supporting stents are used in other body lumens such as biliary, colorectal, esophageal, ureteral and urethral tract, and upper airway. Aneurysm sealing stents are used to close off potentially dangerous aneurysms or pseudo aneurysms throughout the vascular and non-vascular system.

Percutaneous transluminal angioplasty (PTA) has evolved over the past 20 years to become a common therapeutic technique for the treatment of peripheral vascular disease. Self-expanding stents are delivered to a desired site mounted onto a stent delivery catheter and are held in place on the catheter by an outer cover until the stent has reached the deployment site. The outer cover is retracted and the stent expands off the catheter to contact the walls of the lumen, where it is held in place by the chronic outward pressure of the stent against the walls of the lumen.

There are several problems with self-expanding stents currently on the market, including the fact that their design takes into account only their expansion at the site of deployment, without regard to the twisting and bending that the stent must do to navigate blood vessels on the way to the deployment site, which can cause the stent to collapse, resulting in damage to the stent that impairs proper deployment. Additionally, there exists the possibility of the stent foreshortening, displacing or jumping during deployment, causing the stent to be emplaced improperly, requiring removal of the stent and replacement with another.

Therefore, there is an existing need for a self-expanding stent that, irrespective of the insertion site, is capable of enduring the twisting inherent in the delivery process and that evenly expands at the deployment site without foreshortening.

SUMMARY

One aspect of the present application relates to a bidirectional stent, comprising: (1) a cylinder-shaped stent body comprising a plurality of axially arranged rows of struts encircling a central lumen, wherein each of said rows of struts comprises struts inter-connected to form a wave-pattern with alternating peaks and troughs, wherein each peak has a tip and each trough has a bottom, and wherein said rows of struts form one or more row sections and wherein each row section comprises at least one row of struts; (2) non-flex connectors that connect adjacent rows of struts within each row section, wherein each of said non-flex connectors comprises a first end and a second end, wherein said first end is attached to a tip of a peak in a first row of struts, wherein said second end is attached to a tip of a peak in a second row of struts, wherein said first row of struts and said second row of struts are within the same row section and are adjacent to each other, and wherein no non-flex connector is present in a row section containing only one row of struts; and (3) flex connectors that connect adjacent row sections, wherein each of said flex connectors comprises a first end and a second end, wherein said first end is attached to a bottom of a first trough in an edge row of struts of a first row section, said first trough has a first trough amplitude, wherein said second end is attached to a bottom of a second trough in an edge row of struts of a second row section, said second trough has a second trough amplitude, wherein said first row section is adjacent to said second row section, and wherein said stent body is capable of being twisted clockwise or counter-clockwise from one end of said stent body by one-fourth of a turn, or more, without causing deformation of struts and connectors in said stent body.

Another aspect of the present application relates to a bidirectional stent, comprising: (1) a cylinder-shaped stent body comprising a plurality of axially arranged rows of struts encircling a central lumen, wherein each of said rows of struts comprises struts inter-connected to form a wave-pattern with alternating peaks and troughs, wherein each peak has a tip and each trough has a bottom; and (2) a first set of flex connectors that connect a first pair of adjacent rows of struts and a second set of flex connectors that connect a second pair of adjacent rows of struts, wherein each of said flex connectors has an s-shaped connector body with a rotation orientation and connects a tip of a peak in one row of struts in a pair of adjacent rows of struts to a tip of a peak in another row of struts in the same pair of rows of struts, wherein flex connectors in the same set of flex connectors have the same rotation orientation, and wherein said first set of flex connectors have a rotation orientation that is opposite to the rotation orientation of said second set of flex connectors, wherein said cylinder-shaped stent body is capable of reversibly transforming into a peristaltic shape when twisted clockwise or counter clockwise by one-fourth of a turn, or more, without causing permanent deformation of said stent body.

Another aspect of the present application relates to a bidirectional stent, comprising: (1) a cylinder-shaped stent body comprising a plurality of axially arranged row of struts encircling a central lumen; and (2) flex connectors that connect at least two adjacent rows of struts in such a manner that allows said stent body to be twisted clockwise or counter-clockwise from one end of said stent body by half of a turn, or more, without causing deformation of struts and connectors in said stent body.

Another aspect of the present application relates to a bidirectional stent, comprising: (1) a cylinder-shaped stent body comprising a plurality of axially arranged row of struts encircling a central lumen; and (2) flex connectors that connect at least two adjacent rows of struts in such a manner that allows said stent body to be twisted clockwise or counter-clockwise from one end of said stent body by half of a turn, or more, without causing permanent deformation of said stent body.

Another aspect of the present application relates to a method for making the stent of the present application, comprising: slitting a cylinder-shaped tube with a laser to create a matrix of struts and connectors that form a stent body.

Another aspect of the present application relates to a method of using the stent of the present application, comprising: placing the stent of the present application in a treatment site in a compressed state; and enlarging said stent to an expanded state at said treatment site to immobilize said stent in a lumen, wherein said stent can be rotationally twisted in either direction without deformation.

Another aspect of the present application relates to a stent kit, comprising: the bidirectional stent of the present application, instructions for using the stent and optionally, a guidewire.

Further objectives, features and advantages of the invention will be apparent from the following detailed description taken in conjunction with the accompanying drawings.

BRIEF DESCRIPTION OF THE DRAWINGS

For the purposes of this disclosure, unless otherwise indicated, identical reference numerals used in different figures refer to the same component.

DETAILED DESCRIPTION

Figure 1:
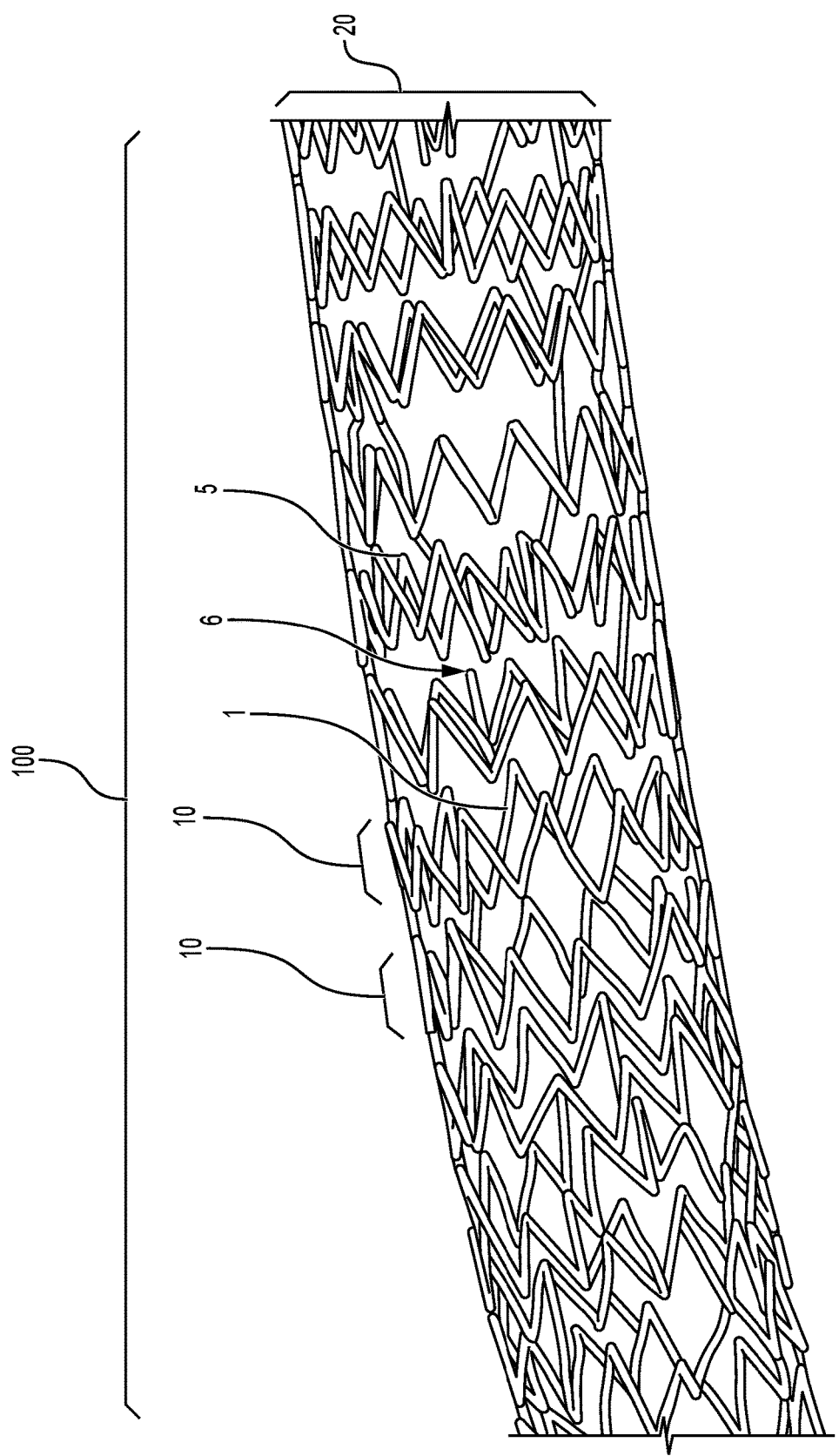
FIG. 1 is a photograph of an embodiment of a bidirectional stent of the present application.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

It is appreciated that certain features of the invention, which are for clarity described in the context of separate embodiments may also be provided in combination in a single embodiment. Conversely various features of the invention, which are for brevity, described in the context of a single embodiment, may also be provided separately and/or in any suitable sub-combination.

One aspect of the present application relates to a bidirectional stent, comprising: a cylinder-shaped stent body comprising a plurality of axially arranged rows of struts encircling a central lumen, wherein each of said rows of struts comprises struts inter-connected to form a wave-pattern with alternating peaks and troughs, wherein each peak has a tip and each trough has a bottom, and wherein said rows of struts form one or more row sections and wherein each row section comprises at least one row of struts; non-flex connectors that connect adjacent rows of struts within each row section, wherein each of said non-flex connectors comprises a first end and a second end, wherein said first end is attached to a tip of a peak in a first row of struts, wherein said second end is attached to a tip of a peak in a second row of struts, wherein said first row of struts and said second row of struts are within the same row section and are adjacent to each other, and wherein no non-flex connector is present in a row section containing only one row of struts; and flex connectors that connect adjacent row sections, wherein each of said flex connectors comprises a first end and a second end, wherein said first end is attached to a bottom of a first trough in an edge row of struts of a first row section, said first trough has a first trough amplitude, wherein said second end is attached to a bottom of a second trough in an edge row of struts of a second row section, said second trough has a second trough amplitude, and wherein said first row section is adjacent to said second row section, wherein said stent body is capable of being twisted clockwise or counter-clockwise from one end of said stent body by one-fourth of a turn, or more, without causing deformation of any struts, non-flex connectors and flex-connectors in said stent body.

In some embodiments each of said flex connectors comprises: a first arm comprising said first end, wherein said first arm has a length that is the same as, or longer than said first trough amplitude; a second arm comprising said second end, wherein said second arm has a length that is the same as, or longer than said second trough amplitude; and a middle section connecting said first arm to said second arm, wherein said middle section forms a first angle with said first arm and a second angle with said second arm, wherein said first angle is in a range of about 90-160 degrees and wherein said second angle is in a range of about 90-160 degrees. In a further embodiment, said first angle is in a range of about 90-120 degrees and wherein said second angle is in a range of about 90-120 degrees.

In another embodiment, each row section contains two or more rows of struts. In a further embodiment each row section contains two rows of struts. In another further embodiment, each row of struts is connected to an adjacent row of struts within the same row section by three or more non-flex connectors.

In another embodiment, the stent body contains three or more row sections. In a further embodiment, each row section is connected to an adjacent row section by three or more flex connectors.

In still another embodiment, peaks in the same row of struts have the same peak amplitude and wherein troughs in the same row of struts have the same trough amplitude.

In yet still another embodiment, each of the non-flex connectors has a length that is smaller than the row width of any of the two rows of the struts connected by said non-flex connector.

In another embodiment the struts, the non-flex connectors and flex connectors are made from a metal or an alloy.

In still another embodiment, said struts, said non-flex connectors and said flex connectors are made from nitinol.

In yet another embodiment, said stent body is coated with a polymeric material. In a further embodiment said polymeric material is a biodegradable material.

In another embodiment, said flex connectors allow said stent body to be twisted clockwise or counter-clockwise from one end of said stent body by ¼ of a turn without causing deformation of any struts and connectors in said stent body.

In still another embodiment, said flex connectors allow said stent body to be twisted clockwise or counter-clockwise from one end of said stent body by ½ of a turn without causing any deformation of said struts in said stent body.

In yet still another embodiment, said flex connectors allow said stent body to be twisted clockwise or counter-clockwise from one end of said stent body by a full turn without causing any deformation of said struts in said stent body.

Another aspect of the present application relates to a bidirectional stent, comprising: a cylinder-shaped stent body comprising a plurality of axially arranged rows of struts encircling a central lumen, wherein each of said rows of struts comprises struts inter-connected to form a wave-pattern with alternating peaks and troughs, wherein each peak has a tip and each trough has a bottom; and a first set of flex connectors that connect a first pair of adjacent rows of struts and a second set of flex connectors that connect a second pair of adjacent rows of struts, wherein each of said flex connectors has an s-shaped connector body with a rotation orientation that connects a tip of a peak in one row of struts in a pair of adjacent rows of struts to a tip of a peak in another row of struts in the same pair of adjacent rows of struts, wherein flex connectors in the same set of flex connectors have the same rotation orientation, and wherein said first set of flex connectors have a rotation orientation that is opposite to the rotation orientation of said second set of flex connectors, wherein said stent is capable of reversibly transforming into a peristaltic shape when twisted clockwise or counter clockwise by one-fourth of a turn, or more, without causing permanent deformation of the stent body.

In some embodiments, each of said plurality of axially arranged rows of struts has a row amplitude and wherein each of said flex connectors has a length that is greater than the row amplitudes of the two rows of struts that are connected by said flex connector. In a further embodiment, each of said flex connectors has a length that is about 150% to 500% of the larger of the row width of the two rows of struts that are connected by said flex connectors. In a still further embodiment, each of said flex connectors has a length that is about 300% of the larger of the row width of the two rows of struts that are connected by said flex connectors.

In another embodiment, said stent body is covered with a biodegradable coating. In a further embodiment, said biodegradable coating comprises chitosan.

Yet another aspect of the present application relates to a bidirectional twistable stent, comprising: a cylinder-shaped stent body comprising a plurality of axially arranged rows of struts encircling a central lumen; and flex connectors that connect at least two adjacent rows of struts in such a manner that allows said stent body to be twisted clockwise or counter-clockwise from one end of said stent body by half of a turn, or more, without causing deformation of said struts in said stent body.

In some embodiments, said stent body can be twisted clockwise or counter-clockwise from one end of said stent body by a full turn without causing deformation of said struts in said stent body.

In other embodiments, said stent body can be twisted clockwise or counter-clockwise from one end of said stent body by two full turns without causing deformation of said struts in said stent body.

Still another aspect of the present application relates to a bidirectional twistable stent, comprising: a cylinder-shaped stent body comprising a plurality of axially arranged rows of struts encircling a central lumen; and flex connectors that connect at least two adjacent rows of struts in such a manner that allows said stent body to be twisted clockwise or counter-clockwise from one end of said stent body by half of a turn, or more, without causing permanent deformation of said stent body.

In some embodiments, said stent body can be twisted clockwise or counter-clockwise from one end of said stent body by a full turn without causing deformation of said struts in said stent body.

In other embodiments, said stent body can be twisted clockwise or counter-clockwise from one end of said stent body by two full turns without causing deformation of said struts in said stent body.

Another aspect of the present invention relates to a method for making a bidirectional stent, comprising: a cylinder-shaped stent body comprising a plurality of axially arranged rows of struts encircling a central lumen, wherein each of said rows of struts comprises struts inter-connected to form a wave-pattern with alternating peaks and troughs, wherein each peak has a tip and each trough has a bottom, and wherein said rows of struts form one or more row sections and wherein each row section comprises at least one row of struts; non-flex connectors that connect adjacent rows of struts within each row section, wherein each of said non-flex connectors comprises a first end and a second end, wherein said first end is attached to a tip of a peak in a first row of struts, wherein said second end is attached to a tip of a peak in a second row of struts, wherein said first row of struts and said second row of struts are within the same row section and are adjacent to each other, and wherein no non-flex connector is present in a row section containing only one row of struts; and flex connectors that connect adjacent row sections, wherein each of said flex connectors comprises a first end and a second end, wherein said first end is attached to a bottom of a first trough in an edge row of struts of a first row section, said first trough has a first trough amplitude, wherein said second end is attached to a bottom of a second trough in an edge row of struts of a second row section, said second trough has a second trough amplitude, and wherein said first row section is adjacent to said second row section, wherein said stent body is capable of being twisted clockwise or counter-clockwise from one end of said stent body by one-fourth of a turn, or more, without causing deformation of any struts, non-flex connectors and flex-connectors in said stent body, said method comprising: slitting a cylinder-shaped tube with a laser to create a matrix of struts and connectors that form the stent body.

In some embodiments, said cylinder-shaped tube is made from a metal or an alloy.

In other embodiments, said cylinder-shaped tube is made from nitinol.

In another embodiment, the method comprises coating said matrix of struts and connectors with a biodegradable polymer coating.

In still another embodiment, the method further comprises covering said matrix of struts and connectors with a biodegradable polymer.

Another aspect of the present application relates to a method of using a bidirectional stent, comprising: a cylinder-shaped stent body comprising a plurality of axially arranged rows of struts encircling a central lumen, wherein each of said rows of struts comprises struts inter-connected to form a wave-pattern with alternating peaks and troughs, wherein each peak has a tip and each trough has a bottom, and wherein said rows of struts form one or more row sections and wherein each row section comprises at least one row of struts; non-flex connectors that connect adjacent rows of struts within each row section, wherein each of said non-flex connectors comprises a first end and a second end, wherein said first end is attached to a tip of a peak in a first row of struts, wherein said second end is attached to a tip of a peak in a second row of struts, wherein said first row of struts and said second row of struts are within the same row section and are adjacent to each other, and wherein no non-flex connector is present in a row section containing only one row of struts; and flex connectors that connect adjacent row sections, wherein each of said flex connectors comprises a first end and a second end, wherein said first end is attached to a bottom of a first trough in an edge row of struts of a first row section, said first trough has a first trough amplitude, wherein said second end is attached to a bottom of a second trough in an edge row of struts of a second row section, said second trough has a second trough amplitude, and wherein said first row section is adjacent to said second row section, wherein said stent body is capable of being twisted clockwise or counter-clockwise from one end of said stent body by one-fourth of a turn, or more, without causing deformation of any struts, non-flex connectors and flex-connectors in said stent body, comprising: placing the stent in a treatment site in a compressed state; and enlarging said stent to an expanded state at said treatment site to immobilize said stent, wherein said stent can be rotationally twisted in either direction at said treatment site without deformation of said stent. In some embodiments, a stent of the present application foreshortens upon deployment less than 1% from its length in its compressed state. In other embodiments, a stent of the present application foreshortens upon deployment less than 0.9, 0.8, 0.7, 0.6, 0.5, 0.4, 0.3, 0.2 or 0.1% from its length in its compressed state.

In some embodiments, said stent can be rotationally twisted at least one quarter turn in either direction at said treatment site without deformation of said stent.

In other embodiments, said stent can be rotationally twisted at least one half turn in either direction at said treatment site without deformation of said stent.

In still other embodiments, said stent can be rotationally twisted at least one full turn in either direction at said treatment site without deformation of said stent.

Still another aspect of the present application relates to a stent kit, comprising: a bidirectional stent, the stent comprising: a cylinder-shaped stent body comprising a plurality of axially arranged rows of struts encircling a central lumen, wherein each of said rows of struts comprises struts inter-connected to form a wave-pattern with alternating peaks and troughs, wherein each peak has a tip and each trough has a bottom, and wherein said rows of struts form one or more row sections and wherein each row section comprises at least one row of struts; non-flex connectors that connect adjacent rows of struts within each row section, wherein each of said non-flex connectors comprises a first end and a second end, wherein said first end is attached to a tip of a peak in a first row of struts, wherein said second end is attached to a tip of a peak in a second row of struts, wherein said first row of struts and said second row of struts are within the same row section and are adjacent to each other, and wherein no non-flex connector is present in a row section containing only one row of struts; and flex connectors that connect adjacent row sections, wherein each of said flex connectors comprises a first end and a second end, wherein said first end is attached to a bottom of a first trough in an edge row of struts of a first row section, said first trough has a first trough amplitude, wherein said second end is attached to a bottom of a second trough in an edge row of struts of a second row section, said second trough has a second trough amplitude, and wherein said first row section is adjacent to said second row section, wherein said stent body is capable of being twisted clockwise or counter-clockwise from one end of said stent body by one-fourth of a turn, or more, without causing deformation of any struts, non-flex connectors and flex-connectors in said stent body; and instructions for using the stent.

In some embodiments, the kit further comprises a guidewire.

Bidirectional Stent

One aspect of the present application relates to a bidirectional stent. Specifically, the stent may be twisted clockwise or counter clockwise by one-fourth of a turn, one-half of a turn, or a full turn without causing deformation of struts and connectors in the stent. As used herein, the term "stent" refers to a device which is implanted within a bodily lumen to hold open the lumen or to reinforce a small segment of the lumen. Stents include vascular and non-vascular stents. Vascular stents are designed for applications in the vascular system, such as arteries and veins. Non-vascular stents are used in other body lumens such as biliary, colorectal, esophageal, ureteral and urethral tract, and upper airway. Non-limiting uses for stents include treating obstructed vessels or lumens; occluding perforations, fistulas, ruptures, dehiscence, punctures, incisions, or aneurysms; and/or for delivering various drugs through controlled release to the particular lumen of interest.

In some embodiments, the bidirectional stent comprises a cylinder-shaped stent body having a plurality of axially arranged rows of struts encircling a central lumen and a plurality of flex connectors. Each of the rows of struts comprises struts inter-connected to form a wave-pattern or zig-zag pattern with alternating peaks and troughs. Each peak has a tip which is the highest point of the peak and defines a peak amplitude for that peak. Each trough has a bottom or nadir which is the lowest point in the trough and defines a trough amplitude for that trough.

As used herein, the term "bidirectional" refers to a stent that is capable of being twisted to the right (i.e., clockwise) and to the left (i.e., counter clockwise) at one end for one-fourth of a turn, one-half of a turn, or a whole turn without causing deformation of the stent structure elements (such as struts and connectors) or without causing permanent deformation of the stent. As used herein "twisted at one end" means to attach one end of a stent to a support and rotate the other end of the stent clockwise or counter clockwise.

As used herein, the term "permanent deformation" or "irreversible deformation" refers to a torsion-induced deformation of a stent structure that is not reversible (i.e., returning to the pre-torsion form) after the removal of the torsion.

As used herein, the term "peak amplitude" refers to the vertical distance between the tip of a peak and the nadir of an adjacent trough. If the two troughs flanking a peak have different depth, the "peak amplitude" of that peak is the vertical distance between the tip of the peak and the nadir of the deeper trough flanking that peak.

As used herein, the term "trough amplitude" refers to the vertical distance between the nadir of a trough and the tip of an adjacent peak. If the two peaks flanking a trough have different height, the "trough amplitude" of that trough is the vertical distance between the nadir of the trough and the tip of the higher peak flanking that trough.

As used herein, the "row width" of a row of struts is defined as the greatest amplitude among the peak amplitudes and trough amplitudes in that row of struts.

The rows of struts are connected to each other, either directly or through connectors. At least two adjacent rows of struts are connected by the flex connectors. In some embodiments, adjacent rows of struts are connected alternatively by the flex connectors and by non-flex connectors (e.g., row 1 is connected to row 2 by flex connectors, row 2 is connected to row 3 by non-flex connector element, row 3 is connected row 4 by flex connectors, row 4 is connected to row 5 by non-flex connector element, and so forth). In other embodiments, adjacent rows of struts are connected alternatively by the flex connectors and by direct connection between the two adjacent rows (e.g., row 1 is connected to row 2 by flex connectors, row 2 is connected to row 3 directly, row 3 is connected row 4 by flex connectors, row 4 is connected to row 5 directly, and so forth). In some embodiments, every other row of struts is connected to an adjacent row of struts with flex connect elements.

In some embodiments, rows of struts are connected directly or by non-flex connectors to form row sections. The row sections are connected to each other by flex connectors. In some embodiments, each row section contains 2, 3, 4, 5, 6, 7, 8, 9 or 10 rows of struts and each stent body contains 2, 3, 4, 5, 6, 7, 8, 9, 10 or more row sections.

Suitable materials for the rows of struts, flex and non-flex connectors include, but are not limited to, metal alloys such as nitinol. In some embodiments, the rows of struts, flex connectors and non-flex connectors are made from the same material. In other embodiments, the rows of struts, flex connectors and non-flex connectors are made from different materials.

Trough-to-Trough Flex Connections

In some embodiments, the flex connector element comprises a wire or strut having a first end and a second end. The first end is attached to a bottom of a trough in one of the two adjacent rows of struts, and the second end is attached to a bottom of a trough in another of the two adjacent rows of struts. The flex connector is composed of three sections: a first section that includes the first end and has a length that is equal to, or greater than, the trough amplitude of the trough the first end is attached to; a second section that includes the second end and has a length that is equal to, or greater than, the trough amplitude of the trough the second end is attached to; and a third section that connects the first section to the second section. The third section forms a first angle with the first section and a second angle with the second section. In some embodiments, the first angle is in the range of about 90-160 degrees, 90-140 degrees or 90-120 degrees, and the second angle is in the range of about 90-160 degrees, 90-140 degrees or 90-120 degrees. The first angle can be the same as, or different from, the second angle. In some embodiments, the first angle is about 90, 95, 100, 105, 110, 115, 120, 125, 130, 135, 140 or 145 degrees, and the second angle is about 90, 95, 100, 105, 110, 115, 120, 125, 130, 135, 140 or 145 degrees. In general, the angles are consistent in size and shape in order to allow for the concentric bidirectionality of the twisting of the device in either direction. The flex connectors allow the angles to collapse and fall into the connectors. In some embodiments, all the flex connectors in a stent body have the same total length and/or shape. In other embodiments, the flex connectors in a stent body have different total length and/or shape. In some embodiments, all the flex connectors connecting the same two rows of struts have the same total length and/or shape. As used herein, the term "total length" of a flex connector element is the distance between the first end and the second end of the flex connector element.

In some embodiments, the adjacent rows that are connected by the flex connectors are connected by at least two flex connectors. In certain embodiments, the two adjacent rows are connected by 2, 3, 4, 5, 6, 7, 8, 9 or 10 flex connectors.

In the embodiments with trough-to-trough flex connection, the twistability of the stent body is determined by a combination of factors such as the number of adjacent rows of struts connected by the flex connectors, the number of flex connectors used between two connected rows of struts, the wave-configuration (e.g., the wave length and amplitude) of the rows of struts, the length of each section in each of the flex connectors and the total length and shape of the flex connectors. In some embodiments, the stent body is configured such that the stent body can be twisted clockwise or counter-clockwise from one end by one-fourth of a turn without causing deformation of struts and connectors in the stent body. In other embodiments, the stent body is configured such that the stent body can be twisted clockwise or counter-clockwise from one end by one-half of a turn without causing deformation of struts and connectors in the stent body. In some embodiments, the stent body is configured such that the stent body can be twisted clockwise or counter-clockwise from one end by a whole turn without causing deformation of struts and connectors in the stent body.

In some embodiments, the stent body is configured such that the stent body can be twisted clockwise or counter-clockwise from one end by one-fourth of a turn without causing the deflection of the peaks outward from the body of the stent more than 1, 2, 3, 4, 5, 6, 7, 8, 9 or 10% of the distance of the diameter of the stent. For example, if a stent is 5 mm in diameter, then a 10% outward deflection of a peak would mean that said peak protrudes 0.5 mm from the outside of said stent. In other embodiments, the stent body is configured such that the stent body can be twisted clockwise or counter-clockwise from one end by one-half of a turn without causing the deflection of the peaks outward from the body of the stent more than 1, 2, 3, 4, 5, 6, 7, 8, 9 or 10% of the distance of the diameter of the stent. In some embodiments, the stent body is configured such that the stent body can be twisted clockwise or counter-clockwise from one end by a whole turn without causing the deflection of the peaks outward from the body of the stent more than 1, 2, 3, 4, 5, 6, 7, 8, 9 or 10% of the distance of the diameter of the stent.

The term "non-flex connectors" are connectors that would not contribute to the twistability of the stent body. Examples of non-flex connectors include, but are not limited to, short, straight struts that connect the tips of the peaks in a row of struts to the tips of the peaks in an adjacent row of struts. In some embodiments, two rows of struts are connected directly to each other without the use of connectors by connecting the tip of one or more peaks in one row to the tip of one or more peaks in another row.

Peak-to-Peak Flex Connections

In some other embodiments, at least two pairs of adjacent rows of struts are connected by flex connectors in a peak-to-peak manner. The peak-to-peak flex connector comprises a wire or strut having an offset line profile and a rotation orientation. The offset is the result of a deflection (or jag) to one side or the other at about the mid-point in the length of the flex connector. The deflection is in the same direction in each of the flex connectors within a row. In some embodiments, the offset can only have one of the two rotation orientations: a left rotation orientation (i.e., similar to the profile of the letter "S") or a right rotation orientation (i.e., similar to the profile of the letter "Z"). One end of the peak-to-peak flex connector is attached to a tip of a peak in one of the two adjacent rows of strut, and the other end is attached to a tip of a peak in another of the two adjacent rows of strut. In this configuration, the peak-to-peak flex connector has a total length that is greater than the row width of either of the two rows of struts connected by the peak-to-peak flex connector. In some embodiments, the peak-to-peak flex connector has a total length of about 150-200%, 150-250%, 150-300%, 150-350%, 150-400%, 150-450%, 150-500%, 200-250%, 200-300%, 200-350%, 200-400%, 200-450%, 200-500%, 250-300%, 250-350%, 250-400%, 250-450%, 250-500%, 300-350%, 300-400%, 300-450%, 300-500%, 350-400%, 350-450%, 350-500%, 400-450%, 400-500% or 450-500% of the row width of a row of struts that is connected to the peak-to-peak flex connector.

The peak-to-peak flex connection requires that the peak-to-peak flex connectors connecting a pair of adjacent rows of struts have the same rotation orientation. Further, the stent body must have at least one pair of adjacent rows of struts connected by peak-to-peak flex connectors of left rotation orientation (left-connected pair) and at least one pair of adjacent rows of struts connected by peak-to-peak flex connectors of right rotation orientation (right-connected pair). Preferably, the stent contains an equal number of left-connected pair and right-connected pair so as to offer bidirectional twistability.

In some embodiments, all the flex connectors in the stent body with peak-to-peak connection have the same total length and/or shape. In other embodiments, the flex connectors in a stent body have different total length and/or shape. In some embodiments, all the flex connectors connecting the same two rows of struts have the same total length and/or shape. In some embodiments, the adjacent rows that are connected by peak-to-peak flex connectors are connected by at least two peak-to-peak flex connectors. In certain embodiments, the two adjacent rows are connected by 2, 3, 4, 5, 6, 7, 8, 9 or 10 peak-to-peak flex connectors.

In a stent body containing peak-to-peak flex connectors, twisting the stent body to the left would cause the section of the stent body connected by peak-to-peak flex connectors with left rotation orientation to contract, and the section of the stent body connected by peak-to-peak flex connectors with right rotation orientation to expand. Similarly, twisting the stent body to the right would cause the section of the stent body connected by peak-to-peak flex connectors with right rotation orientation to contract, and the section of the stent body connected by peak-to-peak flex connectors with left rotation orientation to expand. Such contraction and expansion may also results in reversible deformation of one or more flex connectors. The net effect of twisting is to reversibly transform the cylinder-shaped stent into a peristaltic shape with alternating contracted sections and expanded sections. The stent returns to its original cylinder shape when the torsion caused by the twisting is removed.

In the embodiments with peak-to-peak flex connection, the twistability of the stent body is determined by a combination of factors such as the number of adjacent rows of struts connected by the flex connectors, the number of flex connectors used between two connected rows of struts, the wave-configuration (e.g., the wave length and amplitude) of the rows of struts, and the length of the flex connectors. In some embodiments, the stent body is configured such that the stent body can be twisted clockwise or counter-clockwise from one end by one-fourth of a turn without causing irreversible deformation of the stent body and/or irreversible deformation of any struts in the stent body. In other embodiments, the stent body is configured such that the stent body can be twisted clockwise or counter-clockwise from one end by one-half of a turn without causing irreversible deformation of the stent body and/or irreversible deformation of any struts in the stent body. In some embodiments, the stent body is configured such that the stent body can be twisted clockwise or counter-clockwise from one end by a whole turn without causing irreversible deformation of the stent body and/or irreversible deformation of any struts in the stent body, nor any deformation on the shape of the stent body.

Stent Covering or Coating

In some embodiments, a stent of the present application may be covered or coated with a covering or coating material. The stent coating or covering may be applied by any suitable method known in the art, including, but not limited to electrospinning, dip coating, spraying or film coating. In some embodiments, the stent may first be coated with a first layer using one method, followed by coating with one or more additional layers using the same, or a different method. In some embodiments, the material used for the first layer is the same as the material used for at least one additional layer. In other embodiments, the material used for the first layer is different from the material used for any additional layer.

The process of electrospinning can be carried out by any method known in the art. The method used in the present invention is not to be limited to a single method of electrospinning. Exemplary, non-limiting, processes for electrospinning are described, for example, by Yuan, X et al. (Yuan, X et al. Characterization of Poly-(L-Lactic Acid) Fibers Produced by Melt Spinning. J. Appl. Polym, Sci. 2001, 81:251-260.) and in ZEUS Technical Newsletter, Electrospinning—Fibers at the Nano-scale. 2009 (Zeus Industrial Products, Inc., Orangeburg, S.C.).

In the coating of the device by electrospinning, the device is covered in a way that the fibers cross one another interlocking and forming angles. In one embodiment, the fibers intersect one another at angles with angles from about 1, 5, 10, 15, 20, 25, 30, 35, 40 or 45 degrees to about 45, 50, 55, 60, 65, 70, 75, 80, 85, 90 or 95 degrees. In another embodiment, the fibers intersect one another at angles with angles from about 1 degree to about 95 degrees. In a further embodiment, the fibers intersect one another at angles with angles from about 5 degrees to about 95 degrees. In another embodiment, the fibers intersect one another at angles with angles from about 10 degrees to about 90 degrees.

The fibers are overlapped to allow for the stresses during crimping, loading, and expansion to be borne by all the materials filaments with the stress loads being on the various filaments and their respective angles which allows the distribution of the stresses and the loads in all directions versus a uniform direction which is required for the opening and closing of a cylindrical tube of varying lengths. In one embodiment, the fibers are overlapped a minimum of about 1 time and a maximum of about 1000 times. In a preferred embodiment, the fibers are overlapped a minimum of about 1 time and a maximum of about 500 times. In another preferred embodiment, the fibers are overlapped a minimum of about 2 times and a maximum of about 500 times. Yet in another preferred embodiment, the fibers are overlapped a minimum of about 2 times and a maximum of about 400 times. In still another preferred embodiment, the fibers are overlapped a minimum of about 2 times and a maximum of about 300 times. In a more preferred embodiment, the fibers are overlapped a minimum of about 2 times and a maximum of about 200 times. In a most preferred embodiment, the fibers are overlapped a minimum of 2 times and a maximum of 200 times.

In some embodiments, the stent is covered with a persistent, non-biodegradable polymer material. Examples of suitable non-biodegradable covering materials include, but are not limited to, polyethylene terephthalate (PET), polytetrafluoroethylene (PTFE), polyurethane (PU), silicones, or mixtures thereof.

In other embodiments, the covering of the stent can be made of a biodegradable or bioabsorbable material such as, but not limited to, a poly-(α-hydroxy acid), preferably poly-(L-lactic acid). In a further embodiment, the covering material can be mixed with barium sulphate or other illuminating material to insure proper placement and visibility during the deployment using fluoroscopy, x-ray, or other imaging modalities.

In a particular embodiment, the biodegradable or bioabsorbable material for the covering of the stent is formulated to begin to degrade in no less than 15 days after the device is emplaced in the subject. In another embodiment, the biodegradable or bioabsorbable material for the covering of the stent is formulated to begin to degrade in no less than 30 days after the stent is emplaced in the subject. In a further embodiment, the biodegradable or bioabsorbable material for the covering of the stent is formulated to begin to degrade in no less than 45 days after the stent is emplaced in the subject. In still another embodiment, the biodegradable or bioabsorbable material for the covering of the stent is formulated to begin to degrade in no less than 60 days after the stent is emplaced in the subject. In yet another embodiment, the biodegradable or bioabsorbable material for the covering of the stent is formulated to begin to degrade in no less than 90 days after the stent is emplaced in the subject.

In a certain embodiment, the biodegradable or bioabsorbable material for the covering of the stent is formulated to fully degrade within 90 days after the device is emplaced in the subject. In a further embodiment, the biodegradable or bioabsorbable material for the covering of the stent is formulated to fully degrade within 120 days after the stent is emplaced in the subject. In another embodiment, the biodegradable or bioabsorbable material for the covering of the stent is formulated to fully degrade within 150 days after the stent is emplaced in the subject. In still another embodiment, the biodegradable or bioabsorbable material for the covering of the stent is formulated to fully degrade within 180 days after the stent is emplaced in the subject. In yet another embodiment, the biodegradable or bioabsorbable material for the covering of the stent is formulated to fully degrade within one year after the stent is emplaced in the subject.

In one embodiment, the covering of the stent comprises a copolymer made from 34% lactide, 35% caprolactone, 14% trimethylene carbonate, and 17% glycolide. The copolymer may be deposited on the stent like body by electrospinning or by film coating. The copolymer coating would provide strength retention for 30-60 days and mass absorption in 9-12 months.

Examples of biodegradable polymers include, but are not limited to, polydioxanone, polycaprolactone, polygluconate, poly(lactic acid) polyethylene oxide copolymer, modified cellulose, polyhydroxybutyrate, polyamino acids, polyphosphate ester, polyvalerolactone, poly-ε-decalactone, polylactonic acid, polyglycolic acid, polylactides, polyglycolides, copolymers of the polylactides and polyglycolides, poly-ε-caprolactone, polyhydroxybutyric acid, polyhydroxybutyrates, polyhydroxyvalerates, polyhydroxybutyrate-co-valerate, poly(1,4-dioxane-2,3-one), poly(1,3-dioxane-2-one), poly-para-dioxanone, polyanhydrides, polymaleic acid anhydrides, polyhydroxy methacrylates, fibrin, polycyanoacrylate, polycaprolactone dimethylacrylates, poly-β-maleic acid, polycaprolactone butyl acrylates, multiblock polymers from oligocaprolactonediols and oligodioxanonediols, polyether ester multiblock polymers from PEG and poly (butylene terephthalates), polypivotolactones, polyglycolic acid trimethyl carbonates, polycaprolactone glycolides, poly (γ-ethyl glutamate), poly(DTH-iminocarbonate), poly(DTE-co-DT-carbonate), poly(bisphenol A-iminocarbonate), polyorthoesters, polyglycolic acid trimethyl carbonate, polytrimethyl carbonates, polyiminocarbonates, poly(N-vinyl)-pyrrolidone, polyvinyl alcohols, polyester amides, glycolized polyesters, polyphosphoesters, polyphosphazenes, poly[p-carboxyphenoxy)propane], polyhydroxy pentanoic acid, polyanhydrides, polyethylene oxide propylene oxide, soft polyurethanes, polyurethanes having amino acid residues in the backbone, polyetheresters such as polyethylene oxide, polyalkene oxalates, polyorthoesters as well as copolymers thereof, lipids, carrageenans, fibrinogen, starch, collagen, protein based polymers, polyamino acids, synthetic polyamino acids, zein, polyhydroxyalkanoates, pectic acid, actinic acid, carboxymethyl sulfate, albumin, hyaluronic acid, chitosan and derivatives thereof, heparan sulfates and derivates thereof, heparins, chondroitin sulfate, dextran, β-cyclodextrins, copolymers with PEG and polypropylene glycol, gum arabic, guar, gelatin, collagen N-hydroxysuccinimide, lipids, phospholipids, polyacrylic acid, polyacrylates, polymethyl methacrylate, polybutyl methacrylate, polyacrylamide, polyacrylonitriles, polyamides, polyetheramides, polyethylene amine, polyimides, polycarbonates, polycarbourethanes, polyvinyl ketones, polyvinyl halogenides, polyvinylidene halogenides, polyvinyl ethers, polyisobutylenes, polyvinyl aromatics, polyvinyl esters, polyvinyl pyrrolidones, polyoxymethylenes, polytetramethylene oxide, polyethylene, polypropylene, polytetrafluoroethylene, polyurethanes, polyether urethanes, silicone polyether urethanes, silicone polyurethanes, silicone polycarbonate urethanes, polyolefin elastomers, EPDM gums, fluorosilicones, carboxymethyl chitosans polyaryletheretherketones, polyetheretherketones, polyethylene terephthalate, polyvalerates, carboxymethylcellulose, cellulose, rayon, rayon triacetates, cellulose nitrates, cellulose acetates, hydroxyethyl cellulose, cellulose butyrates, cellulose acetate butyrates, ethyl vinyl acetate copolymers, polysulfones, epoxy resins, ABS resins, EPDM gums, silicones such as polysiloxanes, polydimethylsiloxanes, polyvinyl halogens and copolymers, cellulose ethers, cellulose triacetates, chitosans and copolymers and/or mixtures of the aforementioned polymers.

In a particular embodiment, the stent comprises visibility or opacity technology allowing visualization of the stent using an imaging means or imbedding the covering or strut coating with the same or various drugs or illuminating material. In some embodiments, the visibility or opacity technology comprises tantalum markers. In another embodiment, the covering allows the stent to freely float or to move in a controlled manner under the coating and covering, with the level of restriction depending on the thickness of said covering or coating. In another embodiment, the covering or coating has varying degrees of degradation. If the covering was formed by the electrospinning, the filaments would be intertwined and set with such angles to allow the stent to be crimped and opened as required in normal applications and the degradation could be controlled by the density of the material established by the number of filament crossings and the angles to absorb the load and stresses of opening and closing and anatomical compressions. Furthermore, the material of the support, coating and covering of the stent allow normal body fluids to flow unobstructed. In yet another embodiment, the stent is covered in a single layer, double layer, triple layer or multiple layers depending on the need. The covering can be on the outside of the stent like body, on the inside of the stent like body, or encapsulating the like body.

In another embodiment, the stent comprises a therapeutically effective amount of a therapeutic agent or agents. In particular embodiments, the stent comprises at least one therapeutic agent. In other embodiments, the stent comprises one therapeutic agent or more than one therapeutic agent. In still other embodiments, the stent comprises two, at least two, three, four, or five therapeutic agents. In a particular embodiment, a therapeutic agent comprised on the stent is an analgesic or anesthetic agent. In another particular embodiment, a therapeutic agent comprised on the stent is an antibiotic, antimicrobial, antiviral, or antibacterial agent. In another embodiment, a therapeutic agent comprised on the stent is a thrombotic or coagulant agent. In another embodiment, a therapeutic agent comprised on the stent is an anti-thrombotic or anticoagulant agent.

In certain embodiments, the therapeutic agent is comprised in a pharmaceutical composition formulated for sustained-release. Sustained-release, also known as sustained-action, extended-release, time-release or timed-release, controlled-release, modified release, or continuous-release, employs a pharmaceutically acceptable agent that dissolves slowly and releases the therapeutic agent over time. A sustained-release formulation allows the topical release of steady levels of the therapeutic agent directly at the site where it would be therapeutically effective.

In one embodiment, the pharmaceutical composition is formulated for sustained release by embedding the active ingredient in a matrix of insoluble substance(s) such as acrylics or chitin. A sustained release form is designed to release the therapeutic agent at a predetermined rate by maintaining a constant drug level for a specific period of time. This can be achieved through a variety of formulations, including, but not limited to liposomes and drug-polymer conjugates, such as hydrogels.

In another embodiment, the therapeutic agent is comprised in a pharmaceutical composition formulated for delayed-release, such that the therapeutic agent is not immediately released upon administration. An advantage of a delayed-release formulation is that the therapeutic agent is not released from the stent until the stent has been emplaced in the desired location. In some embodiments, the therapeutic agent is first coated onto the stent and is then coated over with a pharmaceutical composition formulated for delayed-release.

In a particular embodiment, the therapeutic agent is delivered in a vehicle that is both delayed release and sustained release.

In another embodiment, a therapeutic agent comprised on the stent is applied to the exterior surface of the device. A therapeutic agent may be applied to the exterior of the cover or may be mixed or imbedded into the covering material. In some embodiments, the stent may contain an additional coating on its exterior that delays the release of the therapeutic agent or modulates the release of the therapeutic agent over time. In one embodiment, the covering of the stent is further coated with a drug coating that can be eluted to minimize hyperplastic response or to induce closure of the aneurysm.

In another embodiment, a therapeutic agent comprised on the stent is applied to the interior surface of the stent. In further embodiments, therapeutic agents are applied to both the interior and to the exterior surfaces of the stent. Therapeutic agents applied to the interior and exterior surfaces of the stent may be the same or different. As a non-limiting example, a coagulant agent may be applied to the exterior surface of the stent to facilitate the healing of a perforation, while an anti-coagulant may be applied to the interior of the stent to prevent restriction of the flow of bodily fluids and cells through the stent.

In some embodiments, the bidirectional twistable stent of the present application is a self-expanding stent. The stent may be maintained in a compressed state by a wrapper or a restrainer. Upon removal of the wrapper or the restrainer, the stent spontaneously expands to an expanded state that has a central lumen with a diameter that is greater than the diameter of the central lumen in the compressed state.

Kit

Another aspect of the present application relates to a bidirectional stent kit. In some embodiments, the kit comprises one or more bidirectional stents and instructions on how to use the one or more bidirectional stents. In some embodiments, the kit further comprises on or more items selected from the group consisting of guide wires, radial introducer sleeves, guide catheters, access closure devices, dilation balloons, suture materials and cutting instruments.

Method of Making the Stent

Another aspect of the present application relates to a method for making the stent of the present application. The stent of the present application can be laser cut, water jet cut, stamped, molded, lathed or formed with other methods commonly used in the art. In some embodiments, the method comprises the steps of slitting a cylinder-shaped tube with laser to create a matrix of struts and connectors that form the stent body of the present application and coating the stent body with a biodegradable polymer coating. In some embodiments, the cylinder-shaped tube is made from a metal or an alloy, such as nitinol. In some embodiments, the method further comprises the step of coating the stent body with a coating material as describe above. In some embodiments, the coating is a biodegradable polymer coating.

Method of Using the Stent

Another aspect of the present application relates to a method of using the stent. The method comprises the steps of placing the expandable stent of the present application in a treatment site in a contracted state and enlarging the stent to an expanded state at the treatment site to immobilize the stent.

Figure 2:
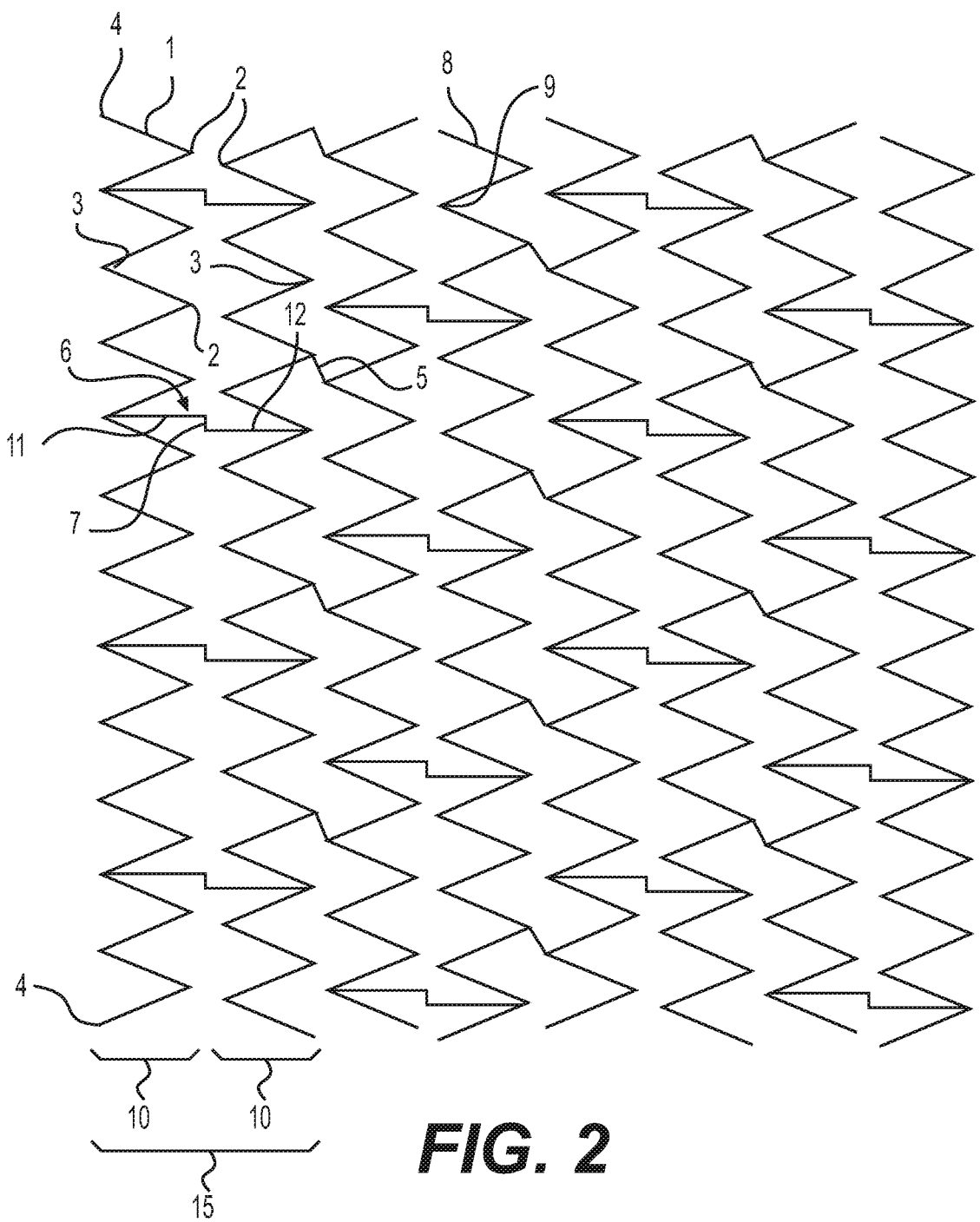
FIG. 2 shows a schematic representation of the strut and connector structure of the stent in FIG. 1.
Figure 3:
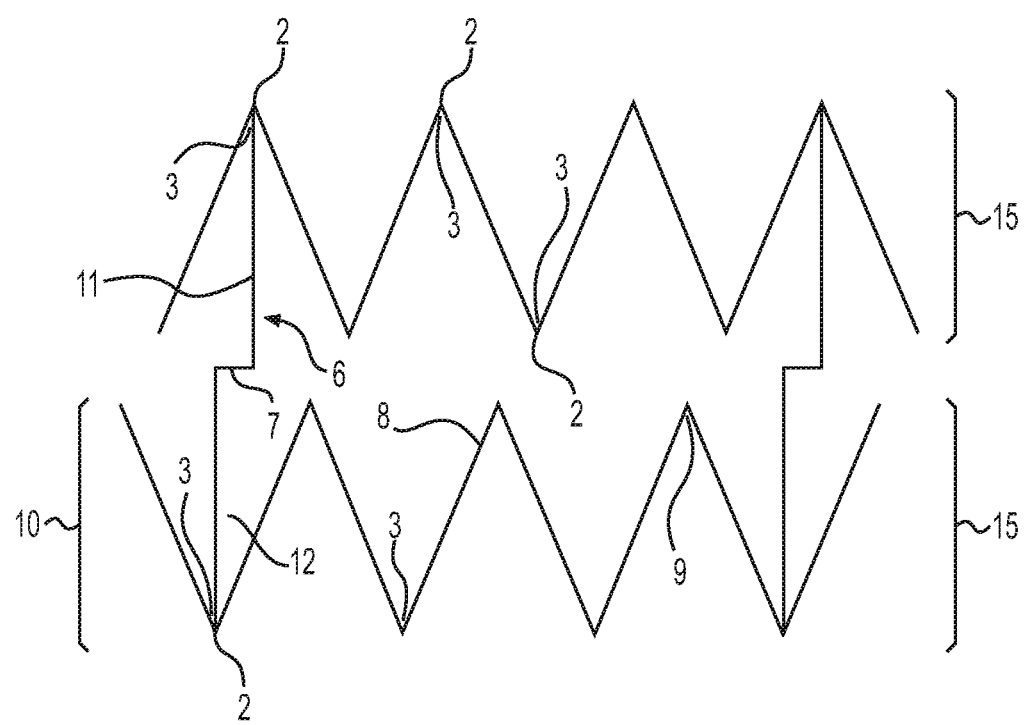
FIG. 3 shows a detailed view of the flex connector of the stent in FIG. 1.

FIG. 1 is a picture of a self-expanding, bidirectional twistable stent 100 of the present application. The stent 100 comprises a stent body 20 that comprises rows 10 of struts 1. Adjacent rows 10 are connected by flex connectors 7 or non-flex connectors 5. FIGS. 2 and 3 are schematic representations showing the matrix of struts 1 and connectors 5, 7 in the stent body. As shown in FIG. 2, the stent body comprise rows 10 of struts 1 that are joined end-to-end in the row 10 to form a wave pattern having alternating peaks 8 and troughs 9. As used herein, the "peak" 8 of each wave is on the outside of the wave pattern of each row 10. Inside each wave, opposite of the tip 2 of the peak 8, is the bottom or nadir 3 of the trough 9. Peaks 8 and troughs 9 face each way in the rows 10. The end 4 of each row 10 is joined to the opposite end 4 of the same row 10, such that each row 10 forms a ring encircling the central lumen of the stent. The rows 10 of struts may be connected to each other by either non-flex connectors 5 or flex connectors 6.

In some embodiments, the flex connectors are aligned in such a way that they allow the troughs to collapse into the flex connector and flex connectors are organized at intermittent patterns alternatively and circumferentially around the stent. In particular embodiments, all flex connectors are aligned going in one direction so that, upon circumferential torsion, all the peaks or troughs line up in the correct grove or saddle. When turned in the opposite direction, the same thing happens but in the opposite direction, wherein the flex connectors in the opposite direction are all aligned in one direction as well.

In some embodiments, each stent body comprises at least one row section 15 of struts. In some embodiments, the row section 15 contains 2 rows 10 of struts. In some embodiments, each row section 15 contains 1 row 10 of struts. In some embodiments, each row section 15 contains 3, 4, 5, 6, 7, 8, or 10 rows 10 of struts. Each row of struts 10 within each row section 15 are joined together by the short, non-flex connectors 5 that are attached to facing peaks 2 of adjacent rows 10 within the row section 15. In some embodiments, there are three connectors 5 joining adjacent rows 10 over the entire length of the rows 10. In other embodiments, there are 4, 5, 6, 7, 8, 9 or 10 non-flex connectors 5 joining adjacent rows 10 over the entire length of the rows 10. In some embodiments, two adjacent rows 10 are joined by a non-flex connector 5 at every third pair of facing peaks 2. In other embodiments, two adjacent rows 10 are joined by a connector 5 at every second, fourth, fifth, sixth, seventh, eighth, ninth or tenth pair of facing peaks 2.

Still referring to FIG. 2 adjacent row sections 15 of stent body 20 are joined to one another by flex connectors 6. In some embodiments, each flex connector 6 is attached at one end to a nadir 3 of a trough in the row 10 at the edge of a section 15, and at the other end to a nadir 3 of a trough in the row 10 at the edge of a facing row sections 15. The flex connectors 6 are designed to absorb the torsional stress of twisting the stent. The length of the flex connectors 6 is such that the peaks 2 along the outside of adjacent row section 15 do not contact each other when the stent is not being twisted. In some embodiments, the flex connector 6 contains a first arm 11, a second arm 12 and a crook or bend 7 that connects the first arm 11 to the second arm 12. The crook 7 is located at the center of each flex connector 6 and forms an angle with the first arm 11 and the second arm 12. In some embodiments, the crook 7 is positioned in the flex connector 6 so that it will clear a peak 2 adjacent to the nadir 3 to which the flex connector 6 is attached when the stent is twisted.

In some embodiments, there are three flex connectors 6 joining adjacent row sections 15 over the entire length of the row section 15. In other embodiments, there are 4, 5, 6, 7, 8, 9 or 10 flex connectors 6 joining adjacent row sections 15 over the entire length of the row section 15. In some embodiments, every third pair of facing nadir 3 at the outer edge of two adjacent row section 15 is connected by a flex connector 6. In other embodiments, every second, fourth, fifth, sixth, seventh, eighth, ninth or tenth pair of facing nadir 3 at the outer edge of two adjacent row section 15 is connected by a flex connector 6.

In some embodiments, each flex connector 6 between two adjacent sections 15 is offset at least one nadir 3 away from the peak 2 to which a non-flex connector 5 joining the rows 10 at the outer edge of said row section 15 to their adjacent rows 10 within said row section 15.

Furthermore, in some embodiments, each flex connector 6 between row section 15 is offset at least one nadir 3 away from the flex connector 6 attached to a nadir 3 on the opposite edge of said row section 15.

Turning now to FIG. 3, shown is a detailed view of a flex connector 6 being joined at each end to a nadir 3 of a row 10 at the edge of a row section 15.

Figure 4:
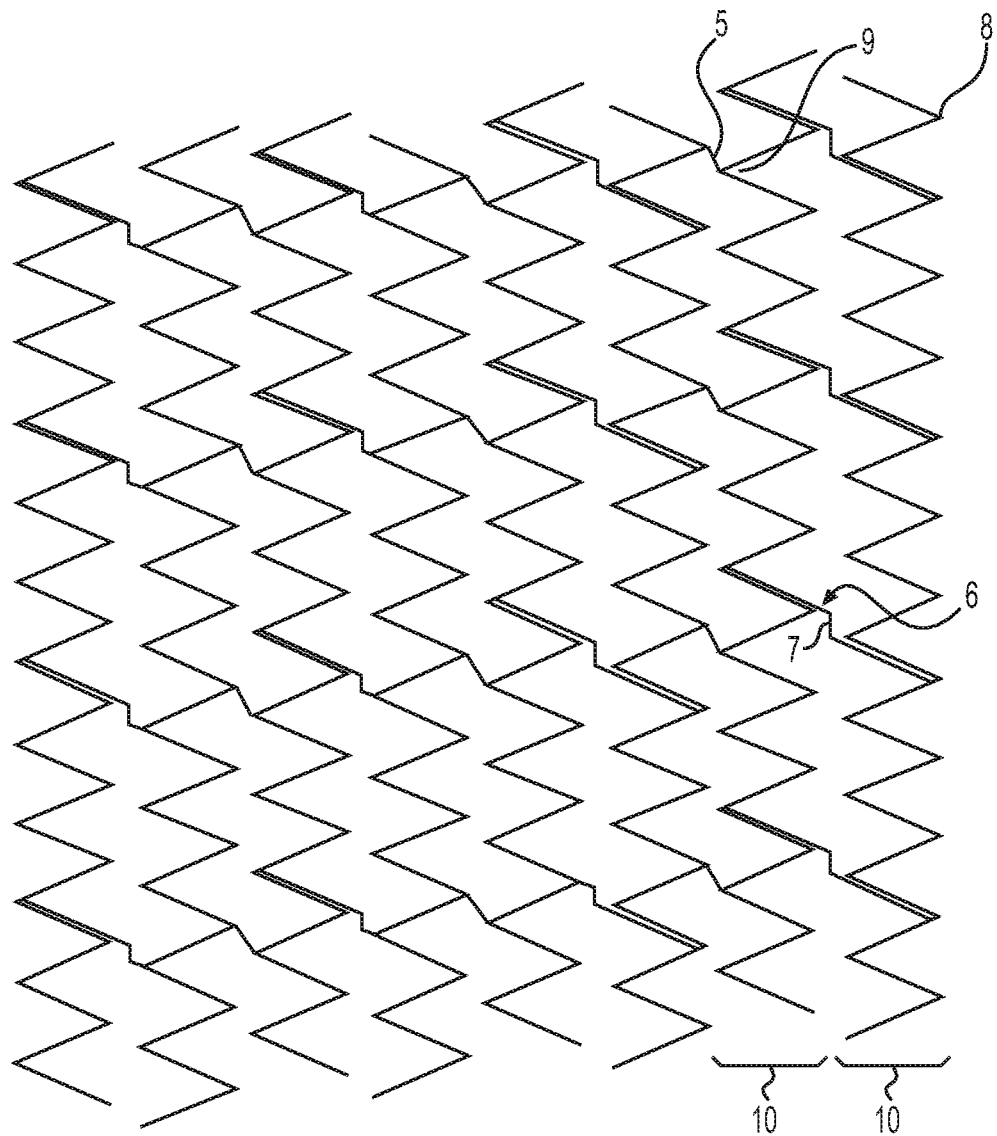
FIG. 4 shows a schematic representation of twisting the stent of FIG. 1 to the left.

FIG. 4 is a schematic representation of the twisting of a stent represented by the schematic shown in FIG. 2. In this case, the stent is twisted in a left-handed direction. Looking at the left-most row 10 in the figure, the flex connector 6 bends to the side such that the crook 7 in the flex connector 6 interdigitates with the peak 2 to the immediate right of the nadir 3 to which it is attached.

Figure 5:
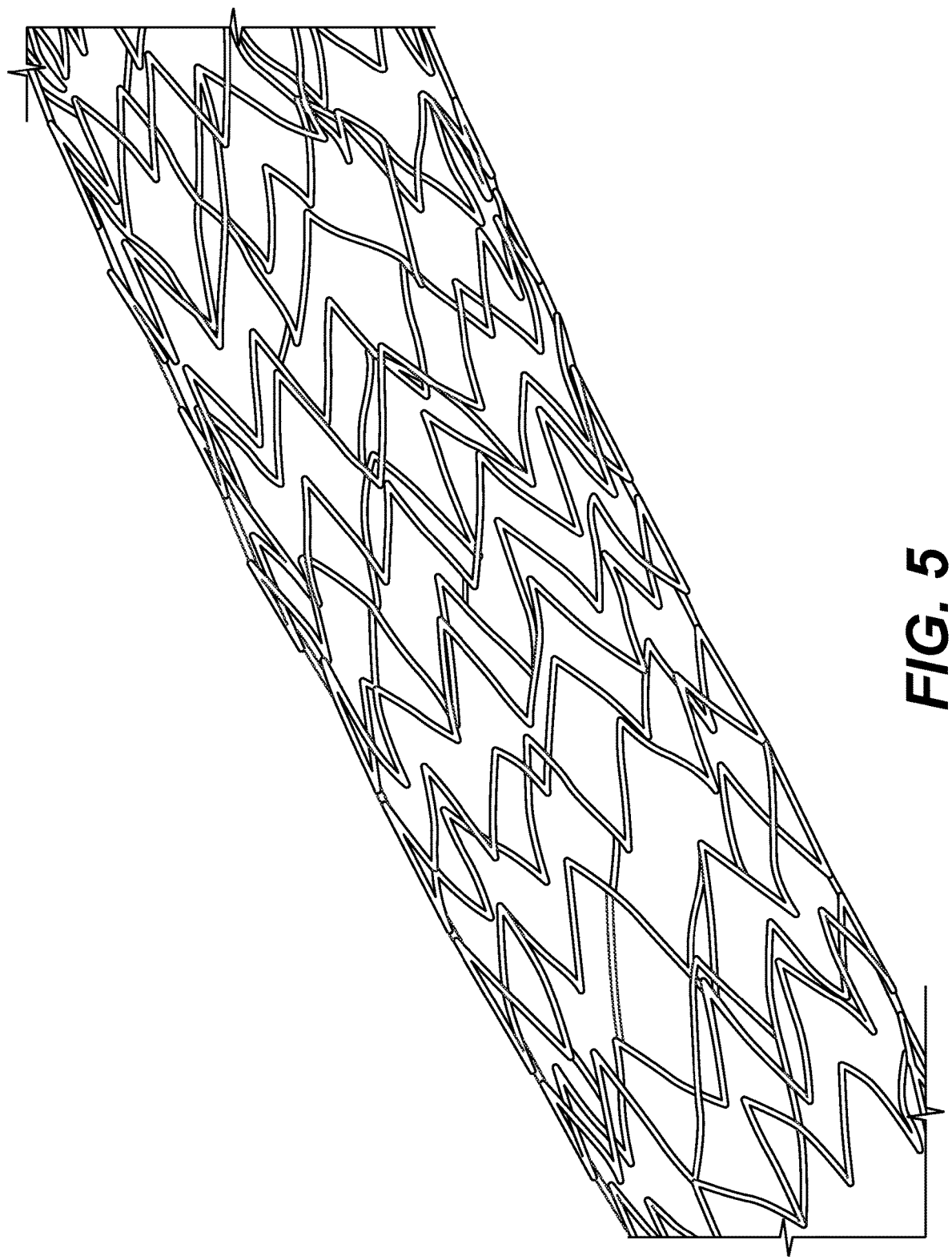
FIG. 5 is a photograph of the stent of FIG. 1 being twisted to the left.

FIG. 5 is a photograph of a stent comprising the structure detailed in the schematic in FIG. 2, twisted in a left-handed manner as described for FIG. 4.

Figure 6:
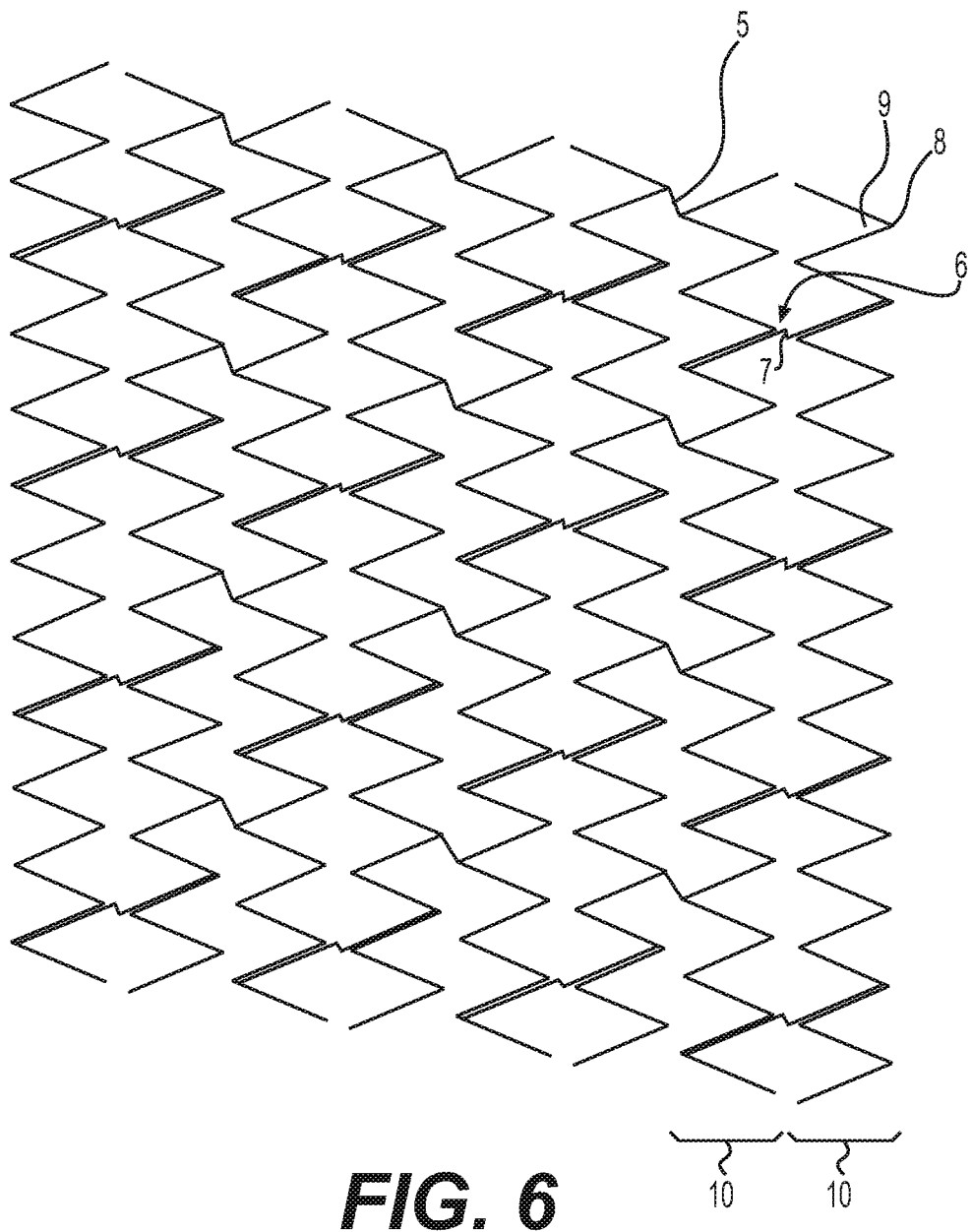
FIG. 6 shows a schematic representation of twisting the stent of FIG. 1 to the right.

FIG. 6 is a schematic representation of the opposite twisting of a stent represented by the schematic shown in FIG. 2. In this case, the stent is twisted in a right-handed direction. Looking at the left-most row 10 in the figure, the flex connector 6 bends to the side such that the crook 7 in the flex connector 6 forms a brace against the peak 2 to the immediate left of the nadir 3 to which it is attached.

Figure 7:
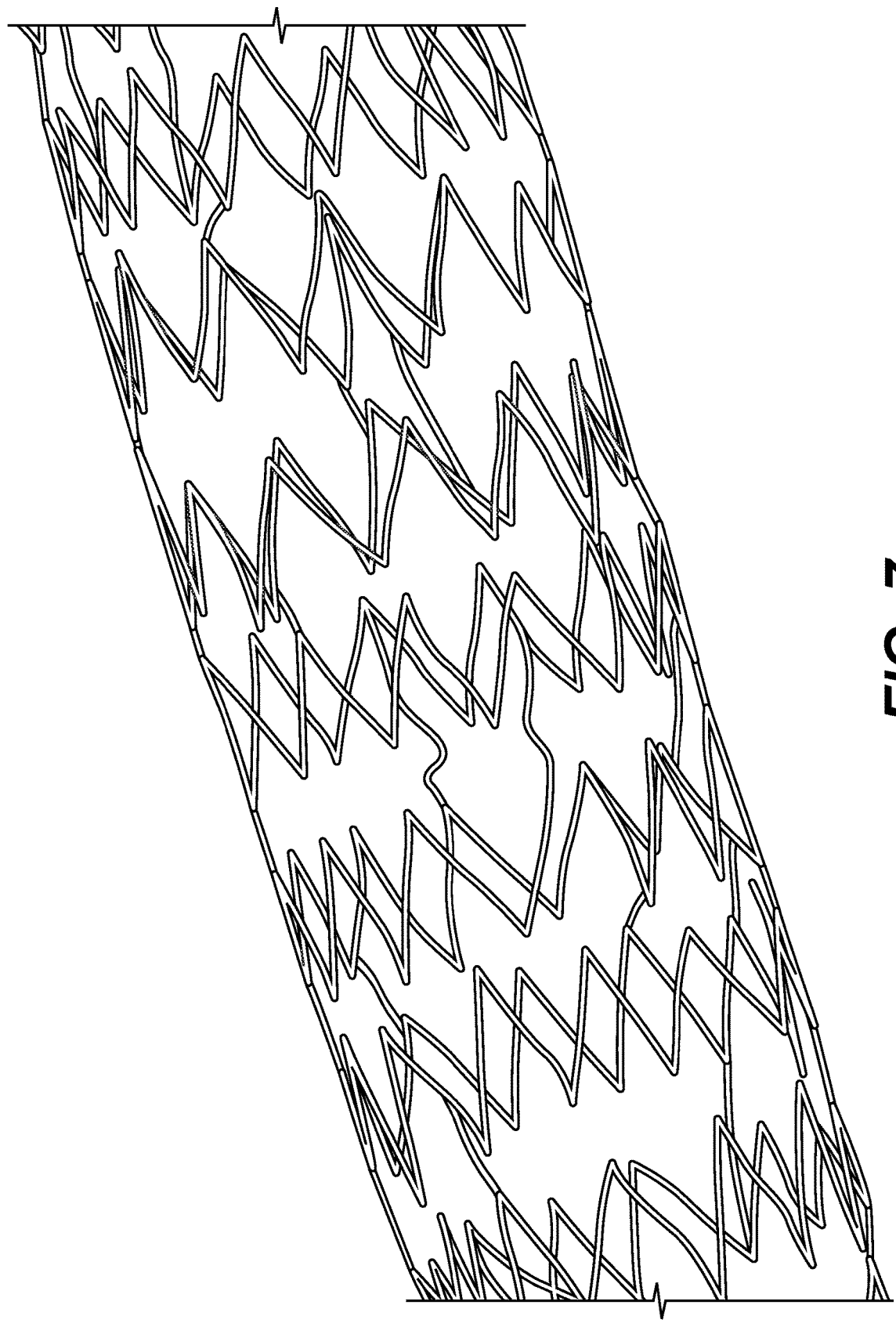
FIG. 7 is a photograph of the stent of FIG. 1 being twisted to the right.

FIG. 7 is a photograph of a stent comprising the structure detailed in the schematic in FIG. 2, twisted in a right-handed manner as described for FIG. 6.

Figure 8A:
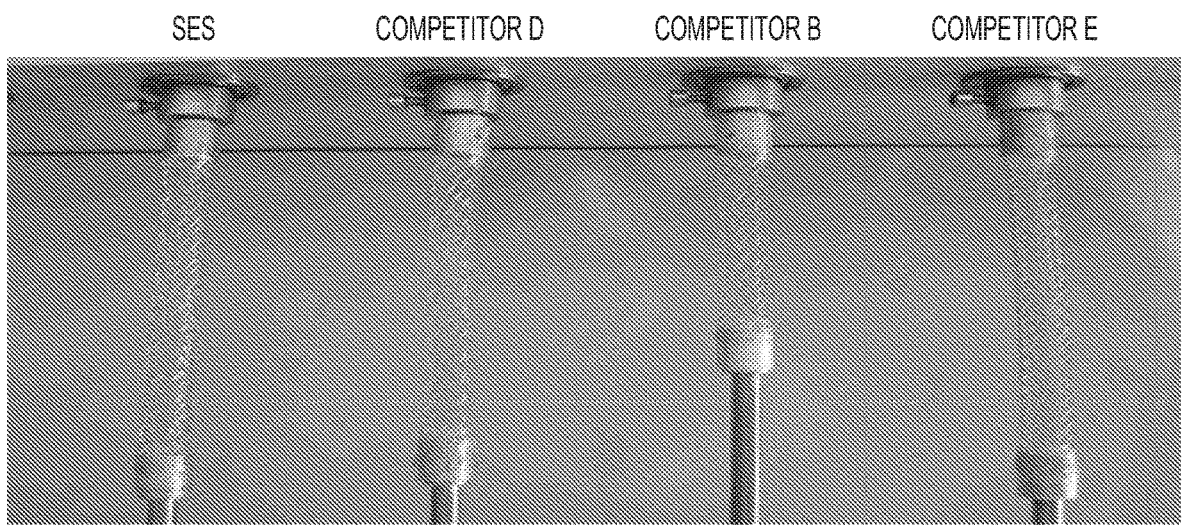
FIGS. 8A-I show the results of a test comparing the bidirectional twistability of the stent of FIG. 1 to the twistability of several commercially available expandable stents.
Figure 8B:
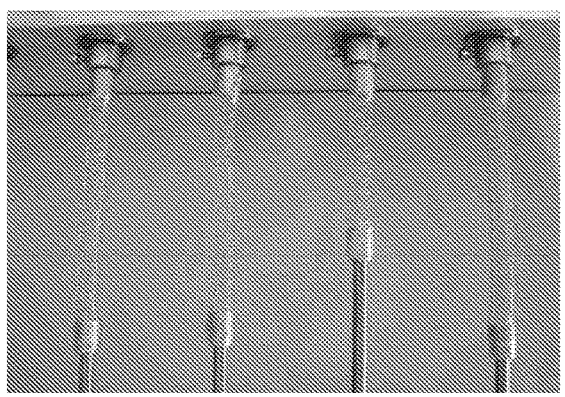

FIGS. 8A-I show a comparison of twistability between a self-expanding stent as described in the present application and 3 expanding stents that are commercially available. The stents are each secured at the top to an immobile base and at the bottom to a turning axle. The axles are linked together and turn the same distance in each figure. FIG. 8A depicts the present stent (SES) and the commercially available stents (Competitor D, Competitor B and Competitor E) in a resting, untwisted state. In FIG. 8B, the axle attached to each of the stents has been turned ¼ turn to the left from the resting position in FIG. 8A, while in FIG. 8C the axle attached to each of the stents has been turned ¼ turn to the right from the resting position in FIG. 8A.

Figure 8C:
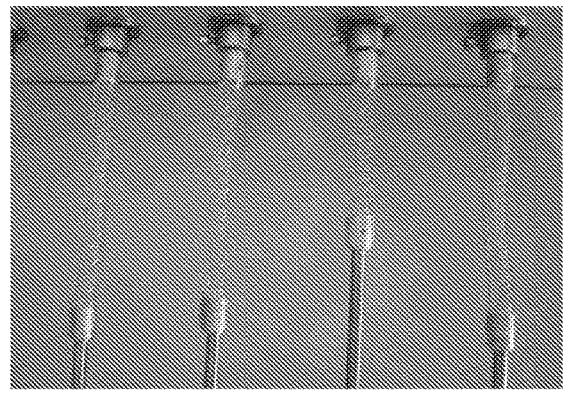
Figure 8D:
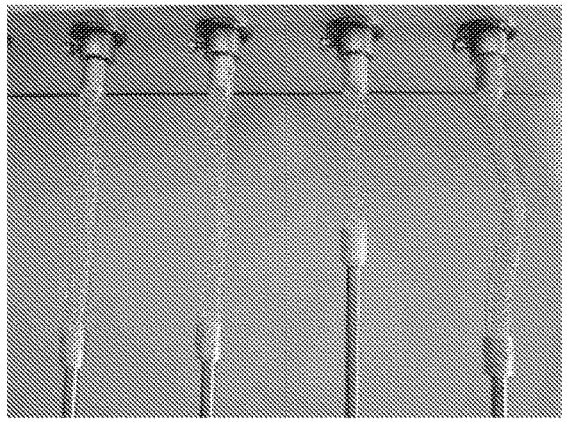
Figure 8E:
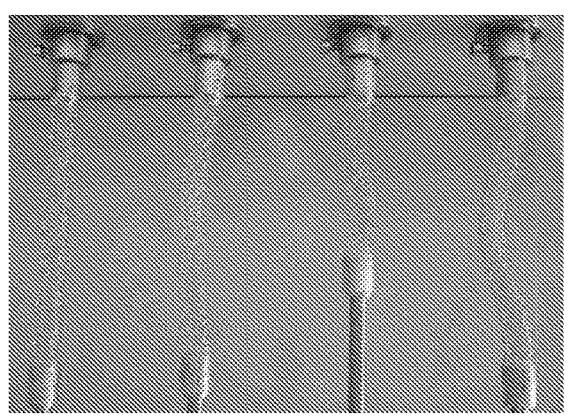

In FIG. 8D, the axle attached to each of the stents has been turned ½ turn to the left from the resting position in FIG. 8A, while in FIG. 8E the axle attached to each of the stents has been turned ½ turn to the right from the resting position in FIG. 8A. As seen in FIGS. 8C and 8D, the stents D, B and E begin to deform from being a straight tube and that this deformation is different for each of stents D, B and E dependent upon whether they are turned towards the left or the right, indicating that there is a unidirectionality to the way each of those stents is designed. However present stent SES is able to turn in either direction with equal ease, showing that the stent is bidirectional in its twistability.

Figure 8F:
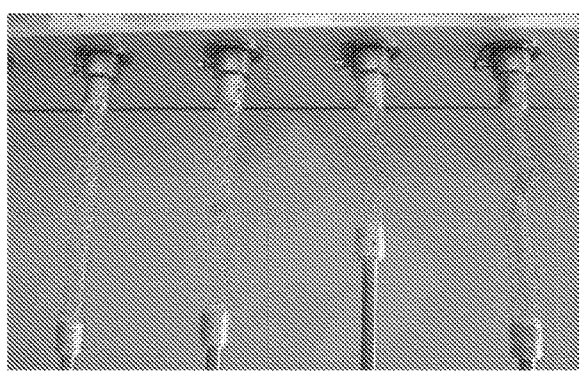
Figure 8G:
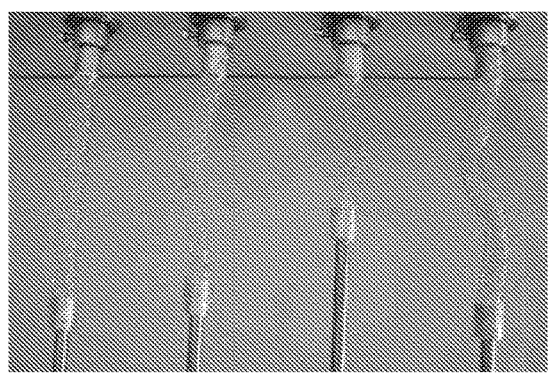

In FIG. 8F, the axle attached to each of the stents has been turned ¾ turn to the left from the resting position in FIG. 8A, while in FIG. 8G the axle attached to each of the stents has been turned ¾ turn to the right from the resting position in FIG. 8A. Each of stents D, B and E deforms or collapses from being a straight tube and the effect is again different for each of stents D, B and E dependent upon whether they are turned towards the left or the right. Accordingly, if these stents are placed in a situation where they are placed under torsional stress, they are likely to fail and will not be able to maintain an open passage. However present stent SES remains able to turn in either direction with equal ease, showing that torsional direction has no effect on its ability to maintain an open passage.

Figure 8H:
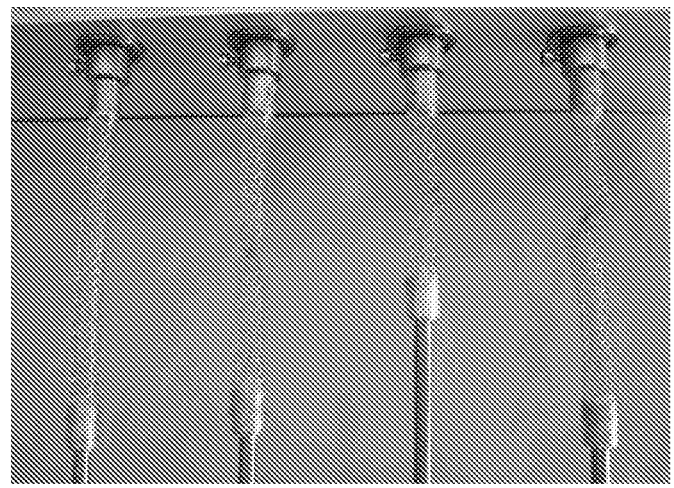
Figure 8I:
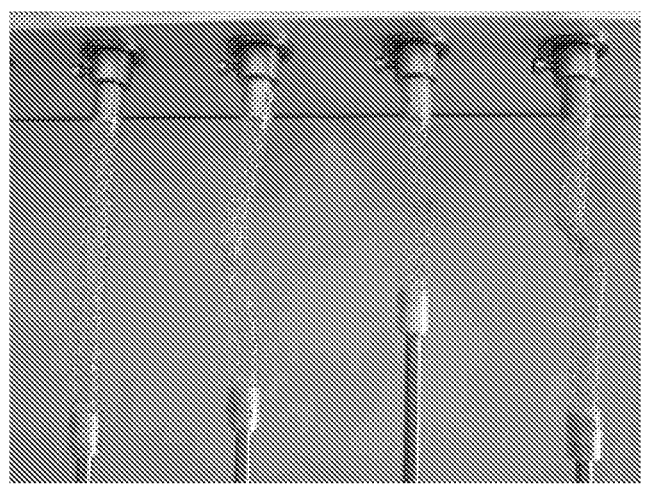

In FIG. 8H, the axle attached to each of the stents has been turned one full turn to the left from the resting position in FIG. 8A, while in FIG. 8I the axle attached to each of the stents has been turned one full turn to the right from the resting position in FIG. 8A. Each of stents D, B and E completely collapses irrespective of whether they are turned towards the left or the right. However present stent SES remains able to turn in either direction with equal ease, showing that torsional direction has no effect on its ability to maintain an open passage.

If a stent is unidirectional, it will perform differently being emplaced through the right arm or leg versus being emplaced through the left arm or leg because the shear stresses of moving through the vessels are different. Furthermore, a unidirectional stent's performance is impacted by which end of the stent is mounted distally on the delivery catheter versus proximally. Therefore, a stent having a unidirectional design must always be loaded onto the catheter in the same direction each time and used in the same arm or leg (only left or only right) to ensure consistent performance. Comparatively, the bidirectional stent of the present application, as shown in FIGS. 8A-I, is resistant to the difference in torsional forces between left-handed and right-handed operation, meaning that a single stent design can be used with equal performance whether inserted on the right side or left side of the patient's body.

Figure 9:
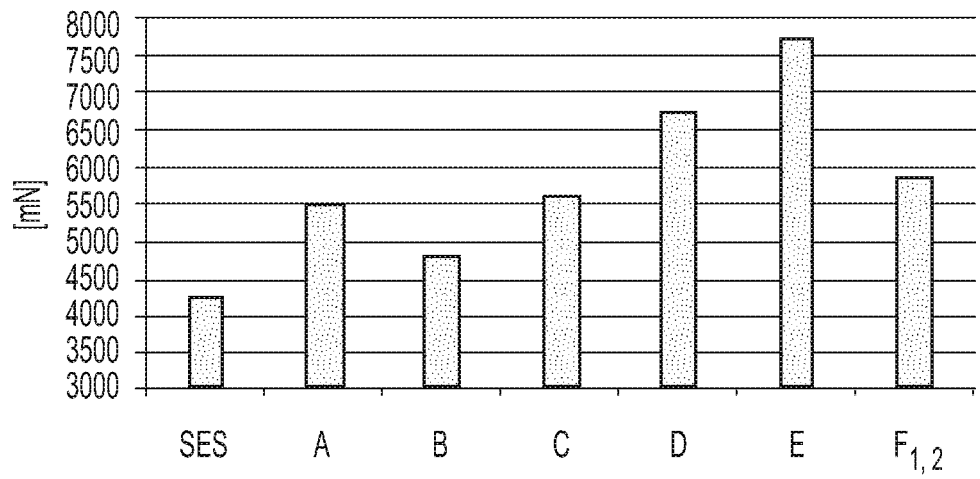
FIG. 9 shows a comparison of the amount of force required to bend the stent of the present application and several commercially available stents.

FIG. 9 depicts the amount of force required in millinewtons (mN) to bend the presently described stent (SES) and commercially available stents A, B, C, D, E, F1 and F2. Greater ease of flexibility allows the stent to be more easily deployed through difficult bends in the vasculature during deployment.

Figure 10:
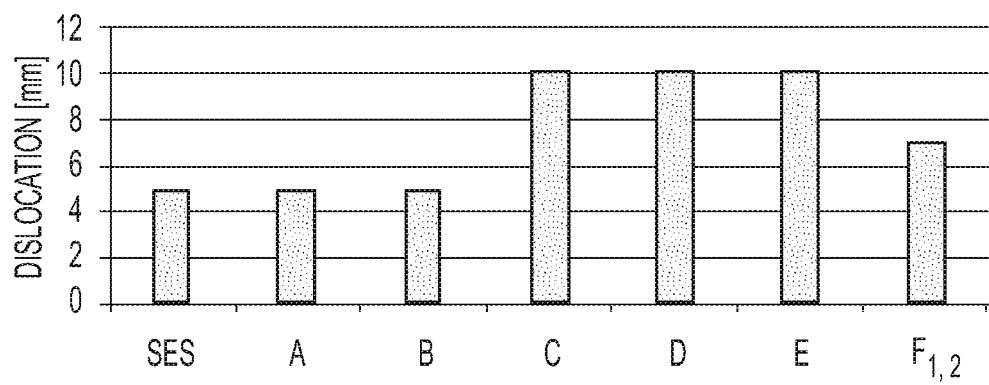
FIG. 10 shows a comparison of the deployment accuracy of the stent of the present application and several commercially available stents.

FIG. 10 depicts the results of a deployment accuracy test of the presently described stent (SES) and commercially available stents A, B, C, D, E, F1 and F2 under identical conditions. The present stent performed as well as or better than the other stents in a measure of dislocation of the stent during deployment, with all segments of the present stent opening uniformly and no overlapping of segments detected.

Figure 11:
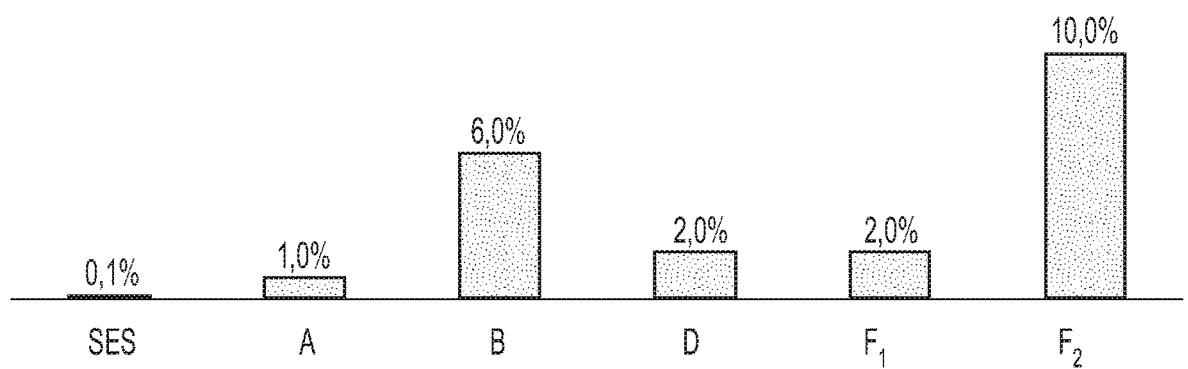
FIG. 11 shows a comparison of the foreshortening of the stent of the present application and several commercially available stents.

FIG. 11 depicts the results of a foreshortening test of the presently described stent (SES) and commercially available stents A, B, D, F1 and F2 under identical conditions. Foreshortening can occur when an expandable stent is deployed from the delivery device, such as a catheter. During delivery, the stent is held in a compressed state on the delivery device. When the stent is released from this compressed state upon deployment, the open spaces between struts expand as the struts move away from one another, with the diameter of the stent changing from the compressed state around the delivery device to an expanded state against the interior walls of the vessel or lumen. As shown in FIG. 11, this stent expansion causes stents A, B, D, F1 and F2 to foreshorten between about 1 and 10% from their length in their compressed state. However, the bidirectional stent of the present application surprisingly foreshortens only about 0.1%, owing to its novel bidirectional design and flex connectors. Accordingly, the placement accuracy of the present stent is higher than other expandable stents. In some embodiments, a stent of the present application foreshortens upon deployment less than 1% from its length in its compressed state. In other embodiments, a stent of the present application foreshortens upon deployment less than 0.9, 0.8, 0.7, 0.6, 0.5, 0.4, 0.3, 0.2 or 0.1% from its length in its compressed state.

Figure 12:
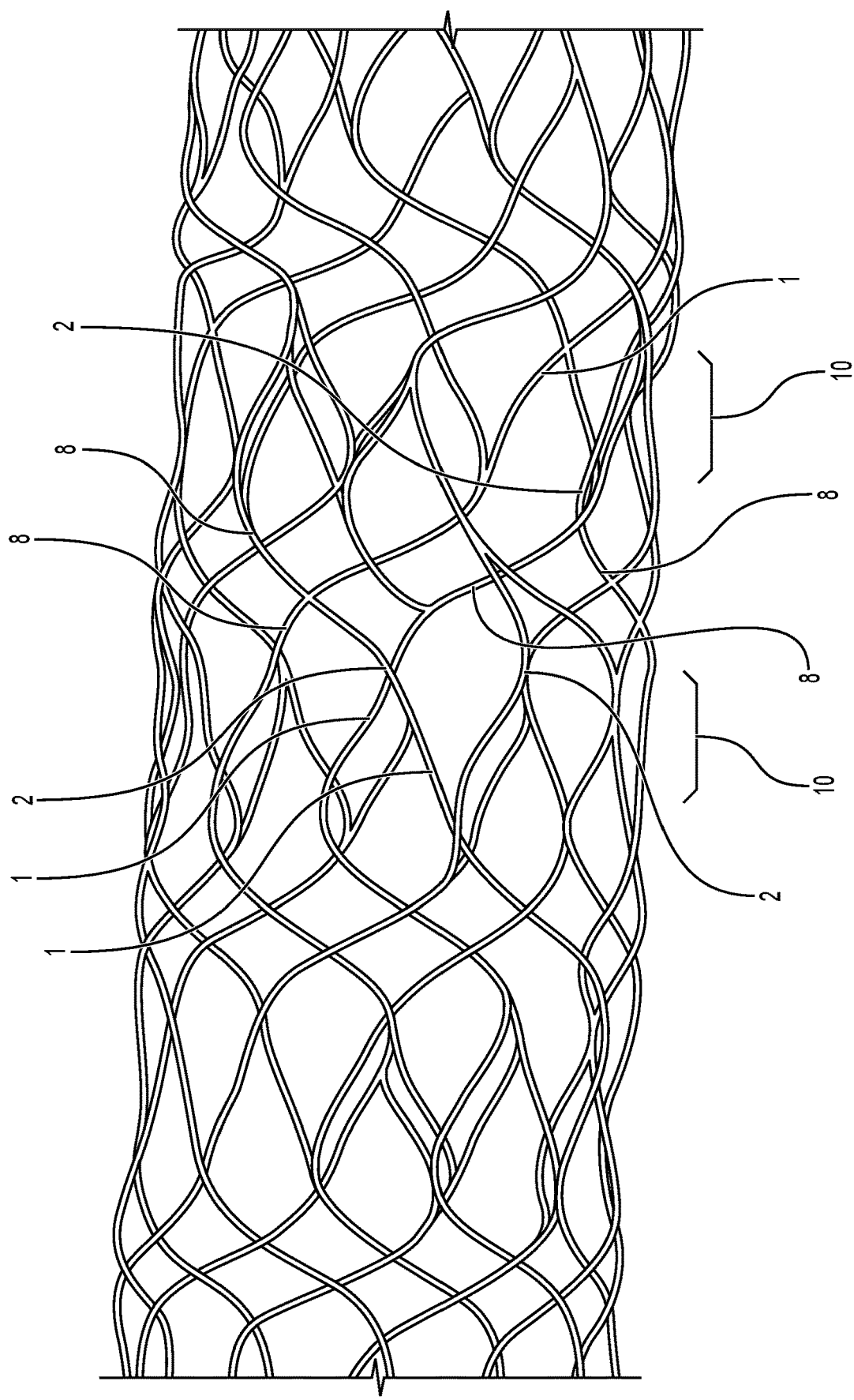
FIG. 12 is a photograph of another embodiment of a bidirectional self-expanding stent of the present application.

FIG. 12 is a photograph of another embodiment of a bidirectional self-expanding stent of the present application, shown in a resting state. This embodiment comprises single rows 10 of struts 1 that are joined end-to-end in the row 10 to form a wave pattern having alternating peaks and troughs. Each row 10 is joined completely around, such that each row 10 forms a ring encircling the central lumen of the stent. In this particular embodiment, each peak 2 (first peak) in a row is attached to one end of a flexible connector 8 that, when the stent is in a resting state, is attached at its other end to a facing peak 2 of an adjacent row 10, with said facing peak 2 being at an angle to the first peak. In some embodiments, said angle is between about 20 degrees and 70 degrees. In some further embodiments, said angle is between about 30 degrees and 60 degrees. In a still further embodiment, said angle is about 45 degrees. When twisted, the openings in this particular embodiment overlap. Depending upon the amount of overlap, the flexibility or pushability of the device can be changed. Further, the length of the struts can be of any length in this embodiment, thus altering the amount of overlap and affording great flexibility and column strength. The interconnected nature of the overlap allows the bidirectional twisting of the stent.

Figure 13:
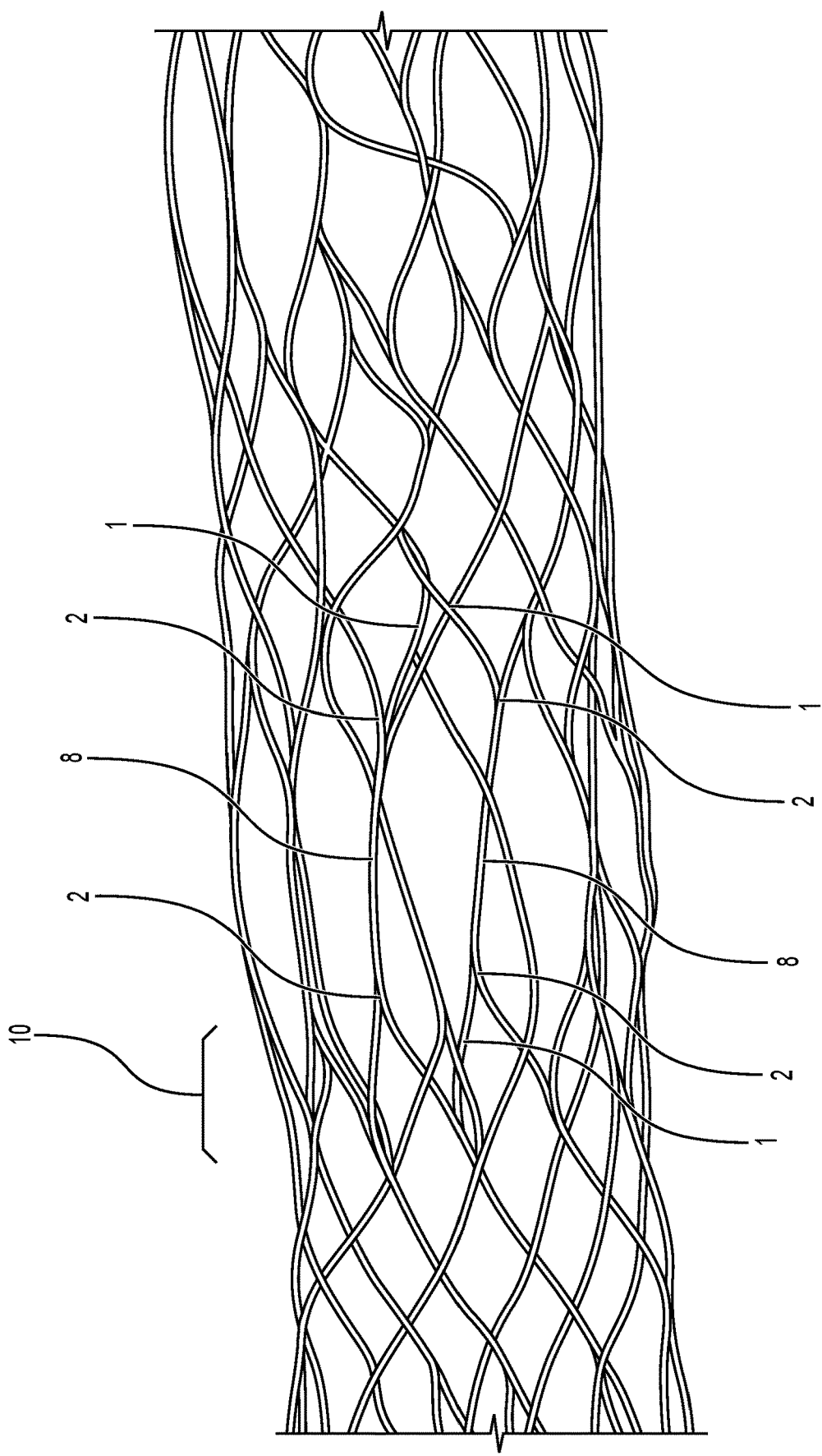
FIG. 13 depicts the stent of FIG. 12 being twisted to the right.

FIG. 13 is a photograph of the embodiment of FIG. 12, wherein the stent has been twisted about ¼ turn to the right and elongated. The figure shows the relationship of the connectnedness of the shapes (formed by the openings) that basically form a line followed by a cell followed by a line throughout the length of the stent. The interconnectedness of this gives it great column strength and allows for removability, while the stacked overlapping allows for changes of flexibility or stiffness based on the amount of the overlap.

Figure 14:
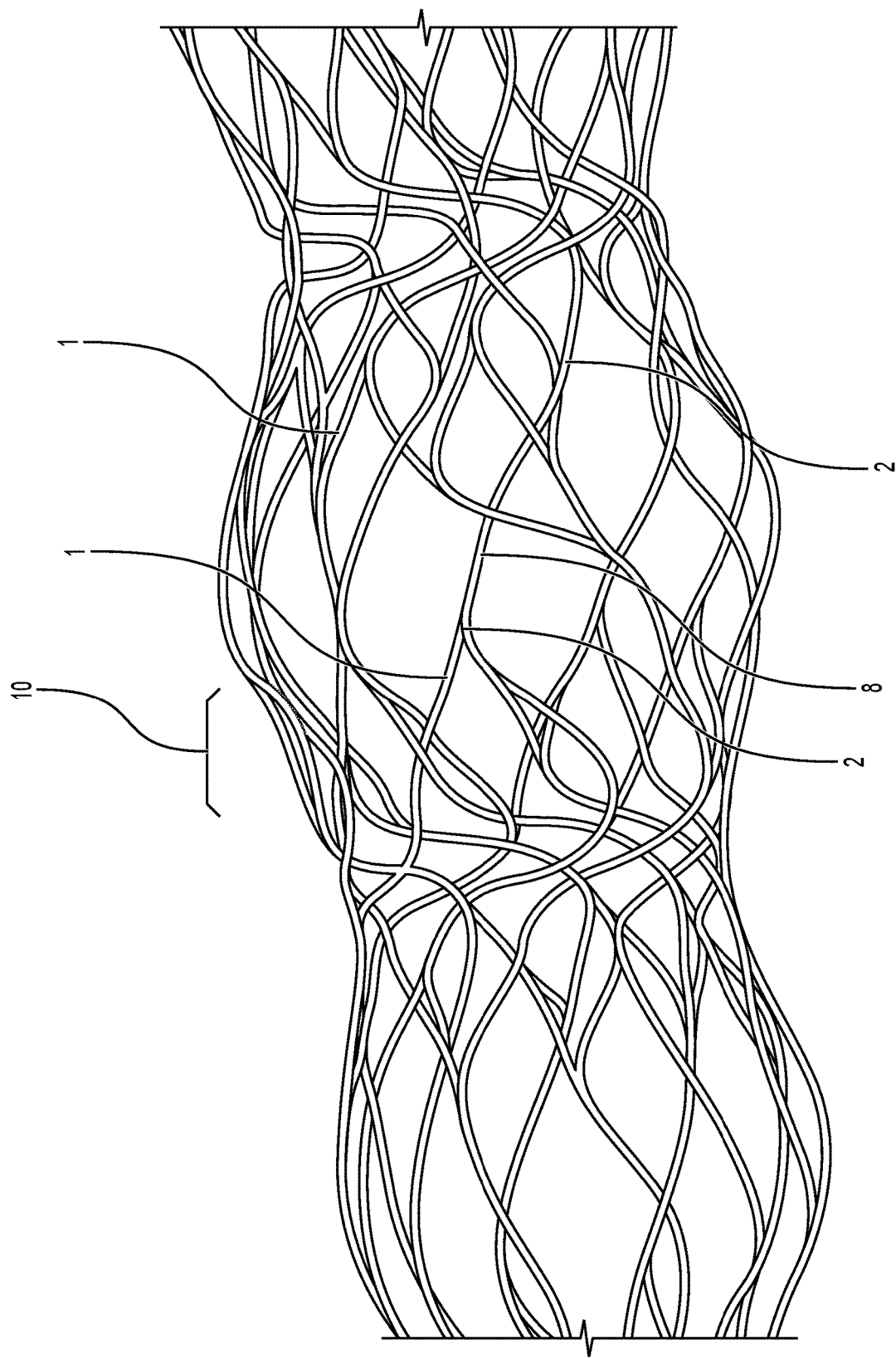
FIG. 14 shows the twisted stent of FIG. 13 with the ends pushed inward

FIG. 14 is a photograph of the embodiment pictured in FIG. 13, wherein the ends of the twisted stent have been pushed towards each other, causing the flexible connectors to bulge outwards. Twisting, pushing and pulling on (or of) sections of the stent are dependent upon the biomechanics of the lumen in which the stent is placed, including (but not limited to) a blood vessel, biliary tree, lung, esophagus, or intestine; as well as being based on the surrounding tissue structure.

Figure 15:
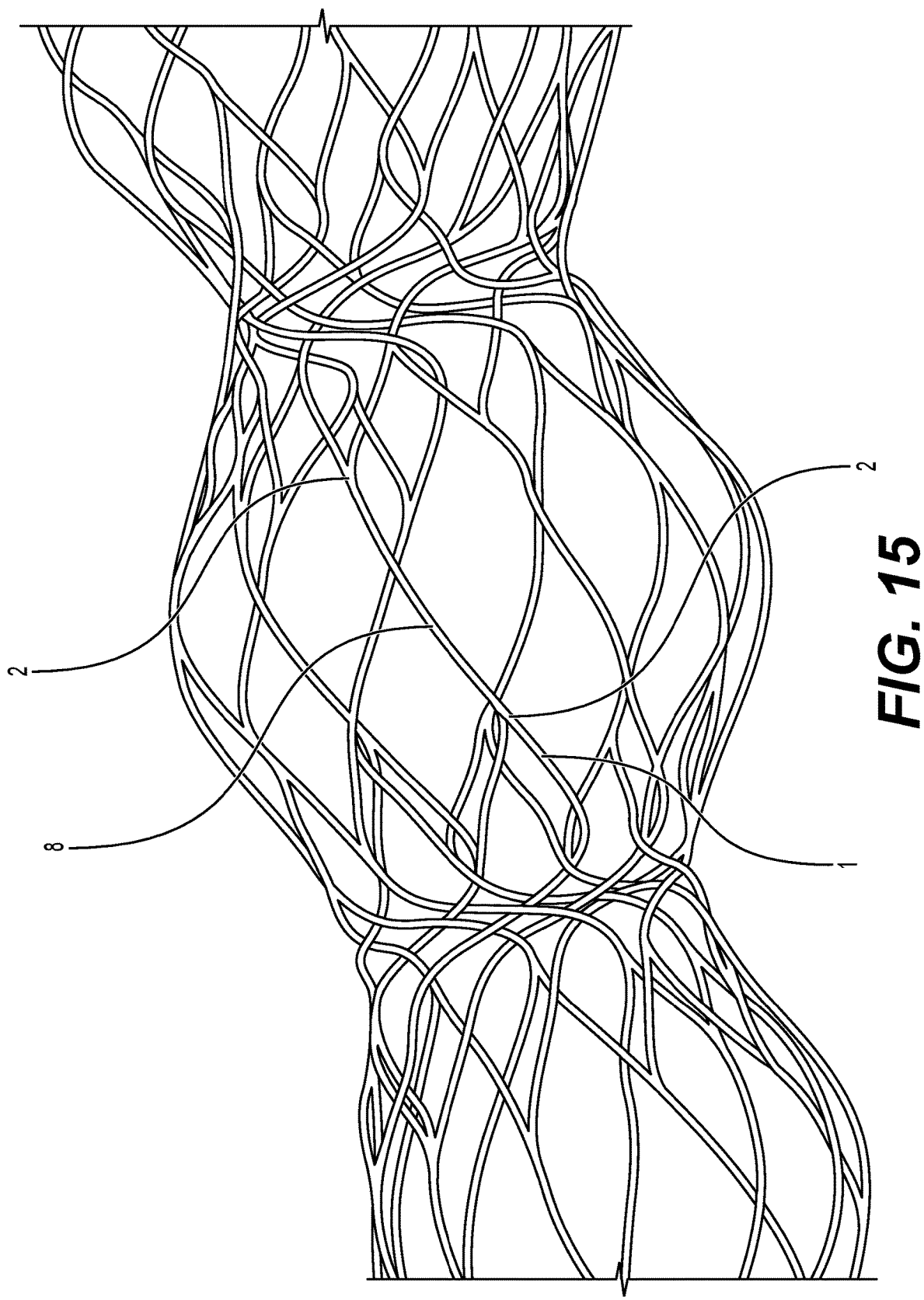
FIG. 15 shows the peristaltic effect of twisting/compressing the stent of FIG. 14.
Figure 16:
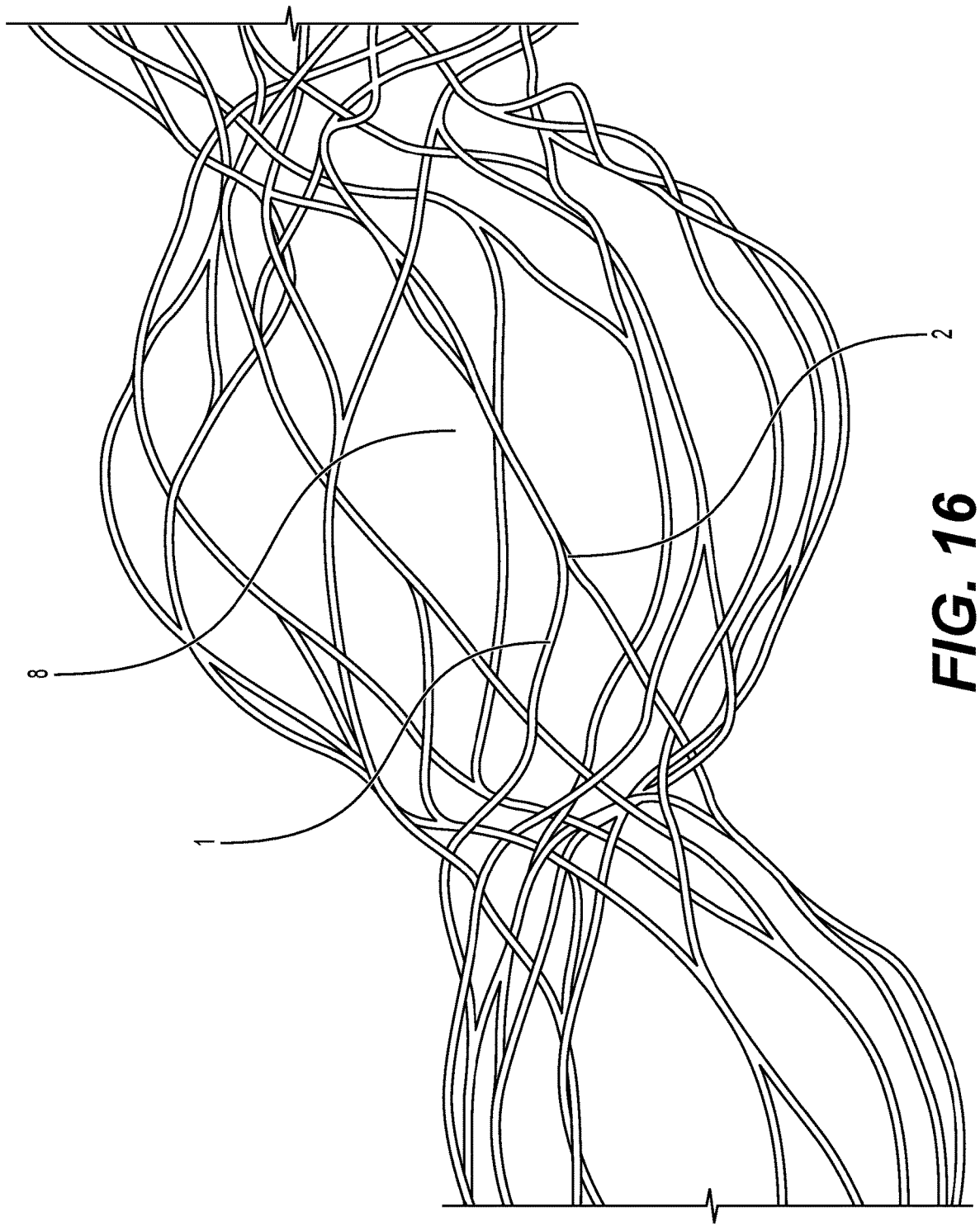
FIG. 16 also shows the peristaltic effect of twisting/compressing the stent of FIG. 14.

FIGS. 15 and 16 show that continued twisting of the stent allow the bulbous sections of the stent to contract and expand, as with a peristaltic motion.

Figure 17:
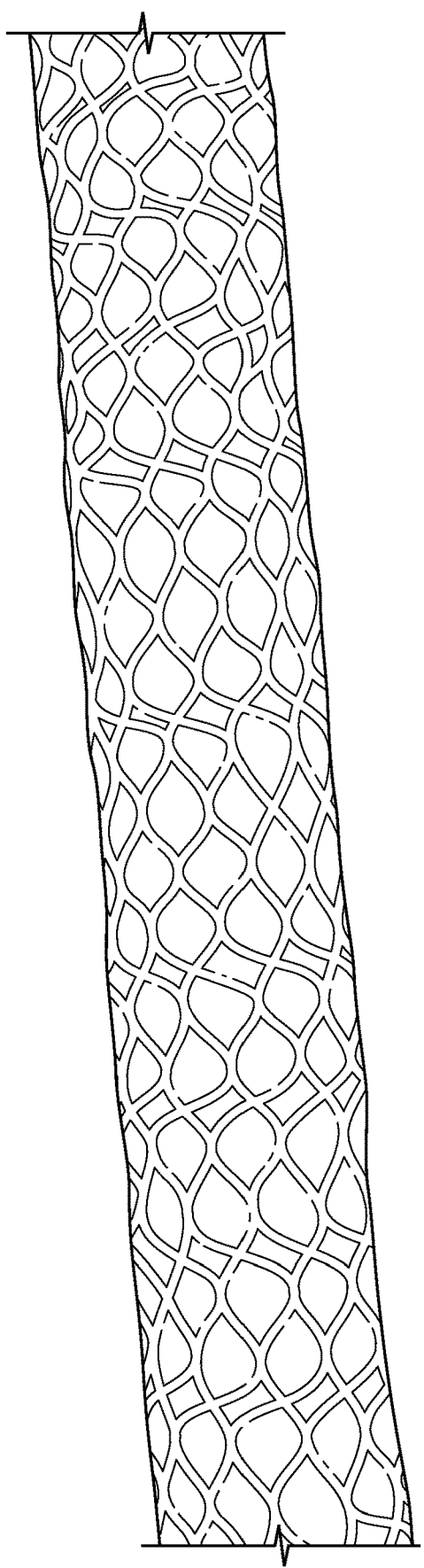
FIG. 17 shows the stent of FIG. 12 with a stretchable electrospun covering.

FIG. 17 shows the embodiment of FIG. 12 with a stretchable electrospun covering.

Figure 18:
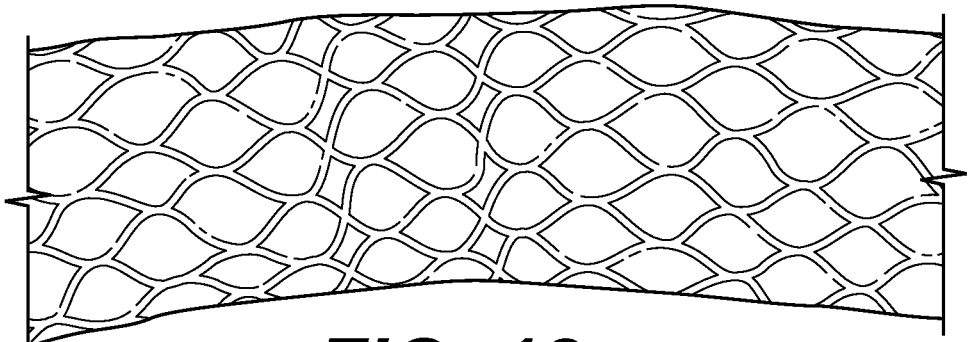
FIG. 18 shows the covered embodiment of FIG. 17 twisted towards the left.

FIG. 18 shows the covered embodiment of FIG. 17 twisted about ¼ turn to the left.

Figure 19:
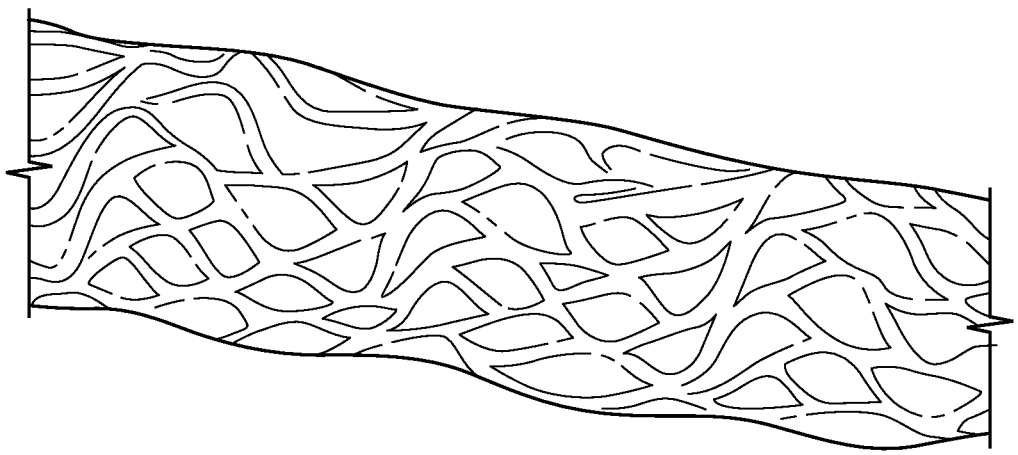
FIG. 19 shows the twisted covered stent of FIG. 18 having the ends of the twisted stent have been pushed towards each other inwards.

FIG. 19 shows the twisted covered embodiment of FIG. 18, wherein the ends of the twisted stent have been pushed towards each other, causing the flexible connectors and the covering to bulge outwards to maintain surface contact. Twisting, pushing and pulling on (or of) sections of the stent are dependent upon the biomechanics of the lumen in which the stent is placed, including (but not limited to) a blood vessel, biliary tree, lung, esophagus, or intestine; as well as being based on the surrounding tissue structure.

Figure 20:
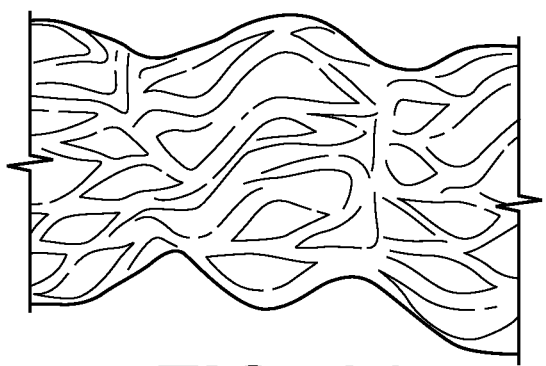
FIG. 20 shows the continued twisting of the covered stent.

FIG. 20 shows that continued twisting of the covered stent allow the bulbous sections of the stent to contract and expand, as with a peristaltic motion.

EXAMPLE 1: DEPLOYMENT OF BIDIRECTIONAL SELF-EXPANDING STENT

An introducer sheath is inserted in an appropriate site in order to gain access to a vessel or lumen.

A guide wire is inserted through the introducer sheath and advanced through the vessel or lumen to span the area where the stent is to be deployed.

The tip of a catheter device is advanced onto the guide wire and the catheter device is advanced through the introducer sheath into the vessel or lumen. The catheter device is advanced through the vessel or lumen such that the tip of the catheter is advanced beyond the deployment site and the stent is directly within the deployment site.

The protective sheath is withdrawn, thereby exposing the stent at the deployment site and expanding the stent against the walls of the lumen.

Following deployment of the stent, the catheter device is withdrawn from the vessel or lumen. The guide wire and introducer sheath are removed and the incision at the entry point is sutured.

EXAMPLE 2: MANUFACTURE OF BIDIRECTIONAL SELF-EXPANDING STENT

The self-expanding bidirectional stents of the present application can be made from nitinol, similar equi-atomic or near equi-atomic intermetallic compounds of nickel and titanium or other superelastic metals or alloys. The stents can be made by any basic process, formed from a slotted tube, laser cut, formed, heat set, deburred and/or polished by any method known in the art for the making or cutting of nitinol stents. In particular embodiments, the self-expanding bidirectional stents of the present application are manufactured with a diameter that is larger than that of the target vessel such that, when the stent self-expands at the target site, it will hold itself in position by pressure against the walls of the lumen.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

It is appreciated that certain features of the invention, which are for clarity described in the context of separate embodiments may also be provided in combination in a single embodiment. Conversely various features of the invention, which are for brevity, described in the context of a single embodiment, may also be provided separately and/or in any suitable sub-combination.

What is claimed is:

1. A bidirectional stent, comprising:
a cylinder-shaped stent body comprising a plurality of axially arranged rows of struts encircling a central lumen and a plurality of axially arranged alternating rows of s-shaped connectors and rows of opposite s-shaped connectors encircling the central lumen,
wherein openings are between each of the s-shaped connectors arranged in alternating rows, and
wherein each row of s-shaped connectors is flanked on both sides by rows of opposite s-shaped connectors and each row of opposite s-shaped connectors is flanked on both sides by rows of s-shaped connectors,
wherein each of said rows of struts consists of struts inter-connected to form a wave-pattern with alternating peaks and troughs, wherein each peak has a tip and each trough has a bottom,
wherein each peak in a row of struts is connected at its tip to a peak at its tip in an adjacent row of struts by an s-shaped connector or opposite s-shaped connector,
wherein said s-shaped connectors in the same row of said s-shaped connectors have the same configuration, and
wherein when the stent is in a resting state, each peak in each row of struts is attached to one end of an s-shaped connector or an opposite s-shaped connector that is attached at its other end to a facing peak of an adjacent row with said facing peak being at an angle to said each peak, and each of said s-shaped connectors or opposite s-shaped connectors has a body having a continuous curve with an inflexion point, and
wherein when said stent is subject to twist, said rows of s-shaped connectors and opposite s-shaped connectors contract or expand in an alternating manner to form a peristaltic shape in said stent body, and said rows of s-shaped connectors or opposite s-shaped connectors that are contracting form a neck shape, and said rows of s-shaped connectors or opposite s-shaped connectors that are expanding form a peristaltic shape, and said neck shape has a lesser radius than the radius of the peristaltic shape at its greatest expanse, thus allowing said stent body to be reversibly twisted clockwise or counter-clockwise from one end of said stent body by a full turn without causing permanent deformation of said struts and said s-shaped connectors or opposite s-shaped connectors in said stent body.

2. The bidirectional twistable stent of claim 1, wherein each of said s-shaped connectors has a length that is about 150% to 500% of the larger of the row width of the two rows of struts that are connected by said s-shaped connectors.

3. The bidirectional twistable stent of claim 2, wherein each of said s-shaped connectors has a length that is about 300% of the larger of the row width of the two rows of struts that are connected by said s-shaped connectors.

4. The bidirectional twistable stent of claim 1, wherein said stent body is covered with a biodegradable coating.

5. The bidirectional twistable stent of claim 4, wherein said biodegradable coating comprises chitosan.

* * * * *